US008834924B2

(12) United States Patent
Yang et al.

(10) Patent No.: US 8,834,924 B2
(45) Date of Patent: Sep. 16, 2014

(54) IMMEDIATE RELEASE FORMULATIONS OF 1-AMINOCYCLOHEXANE COMPOUNDS, MEMANTINE AND NERAMEXANE

(75) Inventors: Yan Yang, Roslyn Heights, NY (US); Rajiv Janjikhel, South Setauket, NY (US); Niranjan Rao, Belle Mead, NJ (US); Antonia Periclou, Jersey City, NJ (US); Wattanaporn Abramowitz, West Windsor, NJ (US); Mahendra G. Dedhiya, Pomona, NY (US); Erhard Seiller, Nidderau (DE); Bernhard Hauptmeier, Gelnhausen (DE)

(73) Assignee: Forest Laboratories Holdings Limited, Hamilton (BM)

( * ) Notice: Subject to any disclaimer, the term of this patent is extended or adjusted under 35 U.S.C. 154(b) by 0 days.

(21) Appl. No.: 13/134,467

(22) Filed: Jun. 8, 2011

(65) Prior Publication Data

US 2011/0236439 A1    Sep. 29, 2011

Related U.S. Application Data

(63) Continuation of application No. 12/410,224, filed on Mar. 24, 2009, now abandoned, which is a continuation of application No. 11/155,319, filed on Jun. 16, 2005, now abandoned.

(60) Provisional application No. 60/581,244, filed on Jun. 17, 2004, provisional application No. 60/636,899, filed on Dec. 16, 2004.

(51) Int. Cl.
*A61K 9/20* (2006.01)
*A61K 9/28* (2006.01)
*A61K 31/13* (2006.01)

(52) U.S. Cl.
CPC . *A61K 9/28* (2013.01); *A61K 31/13* (2013.01); *A61K 9/2846* (2013.01); *A61K 9/2866* (2013.01)
USPC ........................................................ 424/464

(58) Field of Classification Search
None
See application file for complete search history.

(56) References Cited

U.S. PATENT DOCUMENTS 4,122,193 A    10/1978  Scherm et al.
4,273,774 A    6/1981   Scherm
(Continued)

FOREIGN PATENT DOCUMENTS

DE         4014672        11/1991
WO   WO-00/29023 A1       5/2000
(Continued)

OTHER PUBLICATIONS

Summary of Product Characteristics for Merz Memantine tablts; http://ec.europa.eu/health/documents/community-register/2002/200205175237/anx_5237_en.pdf; downloaded Apr. 6, 2011.*

(Continued)

*Primary Examiner* — Nissa Westerberg
(74) *Attorney, Agent, or Firm* — Hueschen and Sage

(57) ABSTRACT

The present invention relates to an immediate release solid oral dosage form containing 1-aminocyclohexanes, preferably memantine or neramexane, and optionally a pharmaceutically acceptable coating, wherein the active ingredient exhibits dose proportionality and is released at a dissolution rate of more than about 80% within about the first 60 minutes following entry of said form into a use environment. The dosage form is direct compressed and has a hardness within the range of between about 3 and about 40 Kp, exhibits an average $T_{max}$ within the range of about 2 to about 8 hours with an active ingredient load within the range of about 2.5 to about 150 mg. The formulation allows for dose-proportional compositions for once daily or b.i.d. dosing, while maintaining a steady average range of $T_{max}$.

19 Claims, 8 Drawing Sheets

(56) References Cited

U.S. PATENT DOCUMENTS

| | | | |
|---|---|---|---|
| 5,061,703 A | 10/1991 | Bormann et al. | |
| 5,248,516 A * | 9/1993 | Wheatley et al. | 427/2.14 |
| 5,334,618 A | 8/1994 | Lipton | |
| 5,373,018 A * | 12/1994 | Cugola et al. | 514/419 |
| 5,382,601 A | 1/1995 | Nurnberg et al. | |
| 5,506,231 A | 4/1996 | Lipton | |
| 5,614,560 A | 3/1997 | Lipton et al. | |
| 5,668,117 A | 9/1997 | Shapiro | |
| 5,827,531 A | 10/1998 | Morrison et al. | |
| 5,866,585 A * | 2/1999 | Fogel | 514/289 |
| 6,007,841 A | 12/1999 | Caruso | |
| 6,034,134 A | 3/2000 | Gold et al. | |
| 6,057,373 A | 5/2000 | Fogel | |
| 6,071,966 A | 6/2000 | Gold et al. | |
| 6,187,338 B1 | 2/2001 | Caruso et al. | |
| 6,194,000 B1 * | 2/2001 | Smith et al. | 424/458 |
| 6,413,556 B1 | 7/2002 | Bathurst et al. | |
| 6,444,702 B1 | 9/2002 | Wang et al. | |
| 6,479,553 B1 | 11/2002 | McCarthy | |
| 2003/0082230 A1* | 5/2003 | Baichwal et al. | 424/470 |
| 2004/0082543 A1* | 4/2004 | Cheung | 514/80 |
| 2004/0102525 A1 | 5/2004 | Kozachuk | |
| 2004/0132826 A1 | 7/2004 | Hirsh et al. | |
| 2004/0224020 A1* | 11/2004 | Schoenhard | 424/471 |
| 2004/0254251 A1* | 12/2004 | Firestone et al. | 514/662 |
| 2005/0014743 A1* | 1/2005 | Gupta et al. | 514/220 |
| 2006/0002999 A1* | 1/2006 | Yang et al. | 424/464 |
| 2006/0051416 A1 | 3/2006 | Rastogi et al. | |
| 2006/0062851 A1 | 3/2006 | Vergez et al. | |
| 2006/0198884 A1 | 9/2006 | Yang et al. | |
| 2007/0270500 A1 | 11/2007 | Dedhiya et al. | |
| 2008/0008743 A1 | 1/2008 | Dedhiya et al. | |

FOREIGN PATENT DOCUMENTS

| | | | |
|---|---|---|---|
| WO | WO 00/29023 A1 | 5/2000 | |
| WO | WO 03/061656 A1 | 7/2003 | |
| WO | WO-03/061656 A1 | 7/2003 | |
| WO | WO 2004/022002 A2 | 3/2004 | |
| WO | WO-2004/022002 A2 | 3/2004 | |
| WO | WO 2004/030633 A2 | 4/2004 | |
| WO | WO-2004/030633 A2 | 4/2004 | |
| WO | WO 2004 056335 | 7/2004 | |

OTHER PUBLICATIONS

Resiberg et al. NEJM 348, p. 1333-1341, Apr. 2003.*
Memantine HCl entry from Drug Facts and Comparisons, p. 1152-1153, 2005.*
STN Registry file for EUDRAGIT(R) L, accessed Apr. 2, 2012.*
Abdoh et al. Pharm Dev Tech, 9(1), p. 15-24, Jan. 2004.*
Ntawukulilyayo et al., International Journal of Pharmaceutics, vol. 121, p. 205-210, 1995.
Wesemann, et al., Distribution and Metabolism of the Potential Anti-Parkinson Drug Memantine in the Human, Journal of Neural Transmission, Suppl. 16, 143-148, 1980.
Tilley, et al., Aminoadamantane Derivatives, Progress in Medicinal Chemistry, vol. 18, 181-184, 1981.
Berkow, The Merck Manual of Diagnosis and Therapy, 1982.
Henkel, et al., Structure-Anti-Parkinson Activity Relationships in the Aminoadamantanes. Influence of Bridgehead Substitution, J. Med. Chem., vol. 25, 51-56, 1982.
Maletta, et al., Organic Mental Disorders in a Geriatric Outpatient Population, Am. J. Psychiatry, vol. 139, No. 4, 521-523, 1982.
Wesemann, et al., Effect of 1-Aminoadamantanes on the MAO Activity in Brain, Liver, and Kidney of the Rat, Translation, Arzneim.-Forsch. Drug Research, vol. 32, No. 1, 1241-1243, 1982.
Prous, J.R. (Pub.) Drugs of Today—Memantine Hydrochloride, Drugs of Today, vol. 19, No. 6, 303-305, 1983.
Terry, et al., Senile Dementia of the Alzheimer Type, Annals of Neurology, vol. 14, No. 5, 497-506, 1983.
Filinson, Diagnosis of Senile Dementia Alzheimer's Type—The State of the Art, Clinical Gerontologist, vol. 2, No. 4, 3-23, 1984.
McKhann, et al., Clinical Diagnosis of Alzheimer's Disease: Report of the NINCDS-ADRDA Work Group Under the Auspices of Department of Health and Human Services Task Force on Alzheimer's Disease, Neurology, vol. 34, 939-944, 1984.
Fungfeld, Experience with Memantine in Treatment of Extrapyramidal and Pyramidal Movement-Disorders, Medizinische Klinki, 80, 20, 559-563, (summary translation p. 562), 1985.
Rote Liste, 64 008 Akatinol® Memantine, 3 pages, 1986, translation.
Fleischhacker, et al., Memantine in the Treatment of Senile Dementia of the Alzheimer's Type, Prog. Neuro-Psychopharmacol. & Psychiat., vol. 10, 87-93, 1986.
Masuo, et al., Effects of Memantine on the Frog Neuromuscular Junction, European Journal of Pharmacology, vol. 130, 187-195, 1986.
Meldrum, et al., Anticonvulsant Action of 1,3-Dimethyl-5-Aminoadamantane, Pharmacological Studies in Rodents and Baboon, Papio Papio, Naunyn-Schmiedergerg's Pharmacol., vol. 332, 93-97, 1986.
Zink, et al., Pschyrembel Clinical Dictionary With Clinical Syndromes and Anatomical Nomenclature—Certified Translation., $115^{th}$ Edition, pp. 1839-1840, 1986.
American Psychiatric Association, Diagnostic and Statistical Manual of Mental Disorders: DSM-III-R, $3^{rd}$ ed. rev., 119-123, 1987.
Gill, et al., Systemic Administration of MK-801 Protects Against Ischemia-Induced Hippocampal Neurodegeneration in the Gerbil, The Journal of Neuroscience, vol. 7, No. 10, 3343-3349, 1987.
Kaplan, et al., Mechanisms of Ischemic Cerebral Injury, Resuscitation, vol. 15, 149-169, 1987.
Kemp, et al., MK-801, NMDA Receptors and Ischaemia-Induced Neurodegeneration, TIPS, vol. 8, 414-415, 1987.
Kemp, et al., Non-Competitive Antagonists of Excitatory Amino Acid Receptors, TINS, vol. 10, No. 7, 1987.
Olney, et al., Anti-Parkinsonian Agents are Phencyclidine Agonists and N-Methyl-Aspartate Antagonists, European Journal of Pharmacology, 142, 319-320, 1987.
Rothman, et al., Excitotoxicity and the NMDA Receptor, Trends in Neuroscience, vol. 10, No. 7, 299-302, 1987.
Ambrozi et al., Treatment of Impaired Cerebal Function in Psychogeriatric Patients with Memantine—Results of a Phase II Double-Blind Study, Pharmacopsychiat. 21, 144-146, 1988.
Choi et al., Glutamate Neurotoxicity and Diseases of the Nervous System, Neuron. vol. 1, 623-634, 1988.
Fungfeld, et al., Dynamic Brain Mapping and Brain Function Monitoring in Geriatric Psychomarmacology—Method for Visualizing Brain Active Drugs. A Early Screening for Prevention of SDAT?, XVIth C.I.N.P. Congress, Munich Aug. 15-19, 1988.
Hahn, et al, Central Mammalian Neurons Normally Resistant to Glutamate Toxicity are Made Sensitive by Extracellular $CA^{2}+$: Toxicity is Blocked by the N-Methyl-D-Aspartate Antagonist MK-801, Proc. Natl. Acad. Sci. USA, vol. 85, 6556-6560, 1988.
Hoyer, Glucose and Related Brain Metabolism in Dementia of Alzheimer Type and its Morphological Significance, Age, vol. 11, 158-166, 1988.
Marcea, et al., Effect of Memantine versus dh-Ergotoxin on Cerebro-Organic Psycho-Syndrome—Translation, Therapiewoche, vol. 38, 3097-3100, 1988.
Moos, et al., Cognition Activators, Medicinal Research Reviews, vol. 8, No. 3, 353-391 (1988).
Seif, et al., Effects of NMDA Antagonists Against Neuronal Damage After Forebrain Ischemia in the Rat, Pharma. of Cerebral Ischemia 1988: Proceedings of the Secon International Symposium on Pharmacology of Cerebral Ischemia Held in Marburg (FRG), pp. 211-215, Oct. 3-5, 1988.
Temple, Results of a Pilot Study Using Two Dose Levels of Memantine in Geriatrics, 1988, Translation.
Wesseman, et al., On the Pharmacodynamics and Pharmacokinetics of Memantine, NIK 6, 1988, Translation.
Bormann, Memantine is a Potent Blocker of N-Methyl-D-Aspartate (NMDA) Receptor Channels, European Journal of Pharmacology, 166, 591-592, 1989.
Katzung (Editor), Absorption of Drugs Into the Body, Basic and Clinical Pharmacology, $4^{th}$ Edition, vol. 4, p. 4, 1989.

(56) References Cited

OTHER PUBLICATIONS

Kornhuber et al., Memantine Displaces [3H]MK-801 at Therapeutic Concentrations in Postmortem Human Frontal Cortex, Journal of Pharmacology, 166, 589-590, 1989.

Schmidt, et al., Anticataleptic Effects of the N-Methyl-D-Aspartate Antagonist MK-801 in Rats, Pharmacol. Biochem. & Behav., vol. 32, No. 3, 621-623, 1989.

Tempel, Can Memantine Improve Disturbances of Social Behaviour and Self-Sufficiency Associated With the Organic Brain Syndrome?, Translation, Therapiewoche, vol. 39, No. 14, 946-952, 1989.

Spraycar, et al. (Editor) Stedmans Medical Dictionary—26th Edition, p. 894, 1995.

Cotran, et al (ed.), Pathologic Basis of Disease, Sixth Edition, p. 1386, 1999.

De Keyser, et al. Clinical Trials with Neuroprotective Drugs in Acute Ischaemic Stroke: Are We Doing the Right Thing?, Trends Neurosci., vol. 22, No. 12, 535-540, 1999.

Winblad, et al., Memantine in Severe Dementia: Results of the 9M-Best Study (Benefit and Efficacy in Severely Demented Patients During Treatment with Memantine), Int. J. Geriat. Psychiatry, 14, 135-146, 1999.

Dichter, et al., Expert Opinion of Dichter and Locke—Clinical Trials in Neuroprotection, Expert opinion Emerging Drugs, vol. 8, No. 1, 267-271, 2003.

Stegman, et al. (Pub.), Stedman's Medical Dictionary, Stedman's Medical Dictionary for the Health Professions and Nursing, 5th Edition, p. 56, 2005.

LaGow, (Ed. Dir.) Physicians Desk Reference—Mechanism of Action and Pharmacodynamics—Namenda, 61 Edition, 1195-1199, 2006.

Wolfe, Shutting Down Alzheimer's, Scientific American, pp. 73-79, 2006.

Parsons, et al., *Neuropharmacology* 1999, 38(6): 735-67.

Chiang, *Acta Anaesthesiologica Sinica* (China (Republic)), 38:31-6 (2000).

Smith, et al., *Society for Neuroscience Abstracts*, 26:695-6 (2000).

Ambrozi, et al., "Treatment of Impaired Cerebal Function in Psychogeriatric Patients with Memantine—Results of a Phase II Double-Blind Study," *Pharmacopsychiat.* 21:144-146 (1988).

American Psychiatric Association, Diagnostic and Statistical Manual of Mental Disorders: DSM-III-R, 3rd ed. rev., pp. 119-123 (1987).

Berkow, The Merck Manual of Diagnosis and Therapy (1982).

Bormann, "Memantine is a Potent Blocker of N-Methyl-D-Aspartate (NMDA) Receptor Channels," *European Journal of Pharmacology*, 166:591-592 (1989).

Buhl, et al., "Frequency of Alzheimer's Disease in a Postmortem Study of Psychiatric Patients," *Danish Medical Bulletin*, vol. 35, No. 3:288-290 (1988).

Chiang, "New Developments in Cancer Pain Therapy," *Acta Anaesthesiologica Sinica* (China (Republic)) 38:31-6 (2000).

Choi, et al., "Glutamate Neurotoxicity and Diseases of the Nervous System," *Neuron.* 1"623-634 (1988).

Cotran, et al (ed.), Pathologic Basis of Disease, Sixth Edition, p. 1386 (1999).

De Keyser, et al. "Clinical Trials with Neuroprotective Drugs in Acute Ischaemic Stroke: Are We Doing the Right Thing?," *Trends Neurosci.* 22:535-540 (1999).

Dichter, et al., "Clinical Trials in Neuroprotection," *Expert Opin. Emerging Drugs*, 8:267-271, (2003).

Filinson, "Diagnosis of Senile Dementia Alzheimer's Type—The State of the Art," *Clinical Gerontologist* 2:3-23 (1984).

Fleischhacker, et al., "Memantine in the Treatment of Senile Dementia of the Alzheimer's Type," *Prog. Neuro-Psychopharmacol. & Psychiat.* 10:87-93 (1986).

Fungfeld, et al., "Dynamic Brain Mapping and Brain Function Monitoring in Geriatric Psychomarmacology—Method for Visualizing Brain Active Drugs. A Early Screening for Prevention of SDAT?," XVIth C.I.N.P. Congress, Munich Aug. 15-19, 1988.

Fungfeld, "Experience with Memantine in Treatment of Extrapyramidal and Pyramidal Movement-Disorders," *Medizinische Klinki*, 80:559-563 (1985), (summary translation p. 562).

Gill, et al., "Systemic Administration of MK-801 Protects Against Ischemia-Induced Hippocampal Neurodegeneration in the Gerbil," *The Journal of Neuroscience* 7:3343-3349 (1987).

Hahn, et al, "Central Mammalian Neurons Normally Resistant to Glutamate Toxicity are Made Sensitive by Extracellular $CA^{2}+$: Toxicity is Blocked by the N-Methyl-D-aspartate Antagonist MK-801," *Proc. Natl. Acad. Sci. USA* 85:6556-6560 (1988).

Henkel, et al., "Structure-Anti-Parkinson Activity Relationships in the Aminoadamantanes. Influence of Bridgehead Substitution," *J. Med. Chem.* 25:51-56 (1982).

Hoyer, "Glucose and Related Brain Metabolism in Dementia of Alzheimer Type and its Morphological Significance" *Age* 11:158-166 (1988).

Kaplan, et al., "Mechanisms of Ischemic Cerebral Injury," *Resuscitation* 15:149-169 (1987).

Katzung, (Editor), "Absorption of Drugs Into the Body," *Basic and Clinical Pharmacology*, 4th Edition, 4:4 (1989).

Kemp, et al., "MK-801, NMDA Receptors and Ischaemia-Induced Neurodegeneration," *Trends in Pharmacological Sciences* 8:414-415 (1987).

Kemp, et al., "Non-Competitive Antagonists of Excitatory Amino Acid Receptors," *TINS* 10:294-298 (1987).

Komhuber, et al., "Memantine Displaces [$^3$H]MK-801 at Therapeutic Concentrations in Postmortem Human Frontal Cortex," *Journal of Pharmacology*, 166:589-590 (1989).

Maletta, et al., "Organic Mental Disorders in a Geriatric Outpatient Population," *Am. J. Psychiatry* 139:521-523 (1982).

Marcea, et al., "Effect of Memantine versus dh-Ergotoxin on Cerebro-Organic Psycho-Syndrome," *Therapiewoche*, 38:3097-3100 (1988).

Masuo, et al., "Effects of Memantine on the Frog Neuromuscular Junction," *European Journal of Pharmacology* 130:187-195 (1986).

McKhann, et al., "Clinical Diagnosis of Alzheimer's Disease: Report of the NINCDS-ADRDA Work Group under the auspices of Department of Health and Human Services Task Force on Alzheimer's Disease," *Neurology* 34:939-944 (1984).

Meldrum, et al., "Anticonvulsant Action of 1,3-Dimethyl-5-Aminoadamantane, Pharmacological Studies in Rodents and Baboon, Papio Papio," *Naunyn-Schmiederqerq's Pharmacol.* 332:93-97 (1986).

Miltner, "Use of Symptomatic Therapy with Memantine in Cerebral Coma," *Arzneim.-Forsch. Drug Research* 32:1268-1270 (1982), (summary translation on p. 1).

Moos, et al., "Cognition Activators," *Medicinal Research Reviews* 8:353-391 (1988).

Olney, et al., "Anti-Parkinsonian Agents are Phencyclidine Agonists and N-Methyl-Aspartate Antagonists," *European Journal of Pharmacology* 142:319-320 (1987).

Parsons, et al., "Memantine is a clinically well tolerated N-methyl-D-aspartate (NMDA) receptor antagonist—a review of preclinical data," *Neuropharmacology* 38:735-67 (1999).

Prous, J.R. (Pub.) Drugs of Today—Memantine Hydrochloride, *Drugs of Today* 19:303-305 (1983).

ROTE LISTE, 64 008 Akatinol® Memantine, 3 pages, 1986.

Rothman, et al., "Excitotoxicity and the NMDA Receptor," *Trends in Neuroscience* 10:299-302 (1987).

Schmidt, et al., "Anticataleptic Effects of the N-Methyl-D-Aspartate Antagonist MK-801 in Rats," *Pharmacol. Biochem. & Behav.* 32:621-623 (1989).

Schneider, et al., "Effects of Oral Memantine on the Parkinson Symptomatology," *DMW* vol. 109, No. 25, (1984), (Certified Translation).

Seif el Nasr, et al., "Effects of NMDA Antagonists Against Neuronal Damage After Forebrain Ischemia in the Rat," Pharma. of Cerebral Ischemia 1988: Proceedings of the Second International Symposium on Pharmacology of Cerebral Ischemia Held in Marburg (FRG), pp. 211-215, Oct. 3-5, 1988.

Smith, et al., "Activity-dependent patterning on NMDA receptor NR1 subunit splice variants in developing ferret visual cortex," *Society for Neuroscience Abstracts*, 26:695-6 (2000).

(56) References Cited

OTHER PUBLICATIONS

Spraycar, et al. (Editor) Stedmans Medical Dictionary—26th Edition, p. 894, 1995.

Stegman, et al. (Pub.), Stedman's Medical Dictionary, Stedman's Medical Dictionary for the Health Professions and Nursing, 5th Edition, p. 56, 2005.

Tempel, "Can Memantine Improve Disturbances of Social Behaviour and Self-Sufficiency Associated With the Organic Brain Syndrome?," *Therapiewoche* 39:946-952 (1989).

Tempel, "Results of a Pilot Study Using Two Dose Levels of Memantine in Geriatrics," 1988 . . . .

Terry, et al., "Senile Dementia of the Alzheimer Type," *Annals of Neurology* 14:497-506 (1983).

Tilley, et al., :Aminoadamantane Derivatives, *Progress in Medicinal Chemistry* 18:1-44 (1981).

Wesemann, et al., "Distribution and Metabolism of the Potential Anti-Parkinson Drug Memantine in the Human," *Journal of Neural Transmission*, Suppl. 16:143-148 (1980).

Wesemann, et al., "Effect of 1-Aminoadamantanes on the MAO Activity in Brain, Liver, and Kidney of the Rat," *Arzneim.-Forsch. Drug Research*, 32:1241-1243 (1982).

Wesemann, et al., "On the Pharmacodynamics and Pharmacokinetics of Memantine," *NIK 6* 1988.

Winblad, et al., "Memantine in Severe Dementia: Results of the 9M-Best Study (Benefit and Efficacy in Severely Demented Patients During Treatment with Memantine)," *Int. J. Geriat. Psychiatry* 14:135-146 (1999).

Wolfe, Shutting Down Alzheimer's, *Scientific American* 294:73-79 (2006).

Zink, et al., Pschyrembel Clinical Dictionary With Clinical Syndromes and Anatomical Nomenclature, 115th Edition, pp. 1839-1840, 1986.

Non-final Office Action dated Feb. 25, 2008 from U.S. Appl. No. 11/155,319.

Non-final Office Action dated Jun. 13, 2008 from U.S. Appl. No. 11/155,319.

Final Office Action dated Sep. 25, 2008 from U.S. Appl. No. 11/155,319.

Miltner, Use of Symptomatic Therapy with Memantine in Cerebral Coma, Translation, Arzneim -Forsch. Drug Research, vol. 32, No. 10, 1268-1270, 1982, English abstract only.

Schneider, et al., Effects of Oral Memantine on the Parkinson Symptomatology—Certified Translation, DMW, vol. 109, No. 25, 1984.

Buhl, et al., Frequency of Alzheimer's Disease in a Postmortem Study of Psychiatirc Patients, Danish Medical Bulletin, vol. 35, No. 3, 288-290, 1988.

Castello, et al., Journal of Pharmaceutical Sciences, 1962, 51, 106-108.

Center for Drug Evaluation and Research; Approval Package for: Application No. 21-487: Clinical Pharmacology and Biopharmaceutcs Review, Oct. 2, 2003.

Eyjolfsson, Drug Development and Industrial Pharmacy, 1998, 24, 797-798.

Guidance for Industry: Waiver for In Vivo Bioavailability and Bioequivalence Studies for Immediate-Release Solid Oral Dosage Forms Based in a Biopharmaceutics Classification System. 2000.

Harmon, et al., Journal of Pharmaceutical Sciences, 2000, 89, 920-929.

Wirth, et al., Journal of Pharmaceutical Sciences, 1998, 87, 31-39.

\* cited by examiner

Dissolution of Tablets with MCC formulation (without Lactose)

IMMEDIATE RELEASE FORMULATIONS OF 1-AMINOCYCLOHEXANE COMPOUNDS, MEMANTINE AND NERAMEXANE

CROSS-REFERENCE TO RELATED APPLICATIONS

This application claims priority under 35 U.S.C. §119, based on U.S. Provisional Application Ser. No. 60/581,244 filed Jun. 17, 2004, and U.S. Provisional Application Ser. No. 60/636,899 filed Dec. 16, 2004, both of which are hereby incorporated by reference in their entirety.

FIELD OF THE INVENTION

The present invention is directed to pharmaceutical solid, oral dosage forms of compositions of 1-aminocyclohexane compounds which exhibit an immediate release profile, possess advantageous stability profiles and additionally disintegrate rapidly in aqueous solutions. The invention is particularly suitable for solid pharmaceutical dosage forms of 1-aminocyclohexane compounds in which a therapeutically effective amount of the active ingredient is available in the use environment shortly after administration. These compositions can be provided as dispersible tablets for administration as aqueous oral solution. In one embodiment, the active ingredient is preferably, the 1-aminocyclohexane, memantine. In another preferred embodiment, the 1-aminocyclohexane is neramexane.

BACKGROUND OF THE INVENTION

1-Aminocyclohexanes, such as Memantine(1-amino-3,5-dimethyladamantane) and neramexane(1-amino-1,3,3,5,5-pentamethylcyclohexane), are moderate affinity, uncompetitive NMDA receptor antagonists with strong voltage dependency and rapid blocking/unblocking kinetics. Therefore, there is an existing and continual need in the art for solid oral formulations of 1-aminocyclohexane compounds, and more preferably memantine HCl (1-amino-3,5-dimethyladamantane hydrochloride) and neramexane mesylate(1-amino-1,3,3,5,5-pentamethylcyclohexane mesylate).

Solid oral drug compositions or preparations have various release profiles such as an immediate release profile as referenced by FDA guidelines ("Dissolution Testing of Immediate Release Solid Oral Dosage Forms", issued August 1997, Section IV-A) or an extended release profile as referenced by FDA Guidelines ("Extended Release Oral Dosage Forms: Development, Evaluation, and Application of In Vitro/In Vivo Correlations", Food and Drug Administration, CDER, September 1997, Page 17). In the dissolution testing guideline for immediate release profiles, materials which dissolve at least 80% in the first 30 to 60 minutes in solution qualify as immediate release profiles. Therefore, immediate release solid dosage forms permit the release of most or all of the active ingredient over a short period of time, such as 60 minutes or less, and make rapid absorption of the drug possible. In contrast, extended release solid oral dosage forms permit the release of the active ingredient over an extended period of time in an effort to maintain therapeutically effective plasma levels over similarly extended time intervals, improve dosing compliance, and/or to modify other pharmacokinetic properties of the active ingredient.

U.S. Pat. No. 5,382,601 provides solid pharmaceutical dosage forms containing memantine, which exhibit an extended two-phase release profile, with a portion of the drug being released immediately, followed by a sustained release of the remainder. The matrix of this formulation contains both a water-soluble and a water-insoluble salt of casein, preferably sodium and calcium caseinate. However, casein has an unpleasant taste; it is associated with the undesirable effect of exacerbating some side effects as disclosed in U.S. Pat. No. 6,413,556; and displays instability in varying pH. Another concern regarding casein is the possibility of Bovine Spongiform Encephalitis (BSE) contamination or transmission of another infectious agent since casein is an animal-derived product.

A general method of preparing modified release N-methyl-D-aspartate (NMDA) receptor antagonists was described in U.S. Pat. No. 6,194,000. This method involves preparing an instant release component and a modified release component to arrive at the final formulation. The patent discloses the formulations consisting of encapsulated beads previously coated using organic solvent-based systems. However, this patent does not specifically disclose compositions containing memantine or neramexane. The patent also does not teach how the release rates affect the $T_{max}$ (time to maximum plasma concentration) or that this procedure will result in dose-proportional formulations.

Currently, a dosing regime of memantine of twice a day is employed using non-dose proportional immediate release tablets. After oral administration in man, memantine is completely absorbed (absolute bioavailability of approximately 100%). The time to maximum plasma concentrations ($T_{max}$) following oral doses of 10 to 40 mg memantine ranged between 3 and 7 hours, with peak plasma concentrations ($C_{max}$) after a single 20 mg oral dose ranging between 22 and 46 ng/mL. The AUC and $C_{max}$ values of memantine increase proportionally with dose over the dosage range of 5 to 40 mg. The elimination half-life ($T_{1/2}$) of memantine is approximately 60-80 hours.

There is a need for dose-proportional memantine formulations which are readily achieved with immediate release formulations. Advantages of immediate release, dose-proportional formulations include improved ease of administration by allowing increases in dose without increasing the number of tablets that need to be administered, and increased flexibility in drug administration by allowing the target drug to be administered either as multiples of lower strength formulations or as one higher strength formulation. Another advantage of dose-proportional formulations of highly soluble and highly permeable drugs, particularly that of memantine and neramexane, is that the bioavailability of multiple strengths, e.g., 10 mg versus 80 mg, are considered identical and in accordance with the guidelines, "Waiver of In Vivo Bioavailability and Bioequivalence Studies for Immediate-Release Solid Oral Dosage Forms Based on a Biopharmaceutics Classification System", U.S. Department of Health and Human Services, Food and Drug Administration. Administration of increasing drug doses are often required as part of an up-titration regimen to the desired therapeutic dose because such regimens result in improved tolerability. In fact, current guidelines for use of memantine in the treatment of Alzheimer's Disease recommend that memantine be administered as a starting dose of 5 mg/day and escalated to the 20 mg/day dose by weekly increases in the dose by 5 mg. Dose proportional formulations are especially important for the treatment of diseases, such as neuropathic pain, which require up-titration to higher doses. The existence of dose proportional, immediate release formulations of different strengths of memantine ranging from 2.5 mg to 80 mg would therefore, allow ease and convenience in dosing during both the up-titration phase and during maintenance at the higher therapeutic dose levels.

SUMMARY OF THE INVENTION

According to the present invention, it has now been found that 1-aminocyclohexanes, such as memantine(1-amino-3,5-dimethyladamantane) and neramexane(1-amino-1,3,3,5,5-pentamethylcyclohexane), and their salts, including the hydrochloride, hydrobromide, mesylate salt as well as other pharmaceutically accepted salts, can be formulated into an immediate release dosage form with dose-proportional bioavailability and advantageous stability profiles where dosage forms preferably disintegrate rapidly.

The formulation of the present invention includes 1-aminocyclohexanes, such as Memantine(1-amino-3,5-dimethyladamantane) and neramexane(1-amino-1,3,3,5,5-pentamethylcyclohexane), an optionally pharmaceutically acceptable coating, and one or more excipients to be administered in a single oral dosage form, preferably once a day. Alternatively, the dosage form may be administered twice a day, with about 4 to about 8 hours between each administration. Preferably, the dosage form is a tablet or an aqueous solution of the dispersed tablet.

Specifically, the present invention provides a dosage form which immediately releases the active agent, for example memantine or neramexane, at a rate of about 80% or more within the first 60 minutes following entry of the dosage form into a use environment. Preferably, the dosage form is released to this extent within the first 30 minutes, more preferably, within the first 15 minutes.

In the present invention, the $T_{max}$ for memantine containing dosage forms is achieved at a time interval averaging from about 3 hours to about 7 hours after entry of the dosage forms into the use environment. Preferably, the time interval averages between about 4 hours to about 6 hours. The $T_{max}$ for neramexane containing dosage forms is achieved at a time interval averaging from about 2 hours to about 8 hours after entry of the dosage form into the use environment. Preferably, the time interval averages between about 3 to about 8 hours.

In specific embodiments where the active ingredient is memantine hydrochloride, the active ingredient of the present invention is usually present in amounts ranging from about 2% w/w to about 20% w/w. Preferably, the amounts range from about 3.2% w/w to about 10% w/w, more preferably from about 3.9% w/w to about 8.4% w/w, based on the weight of the entire dosage form.

In specific embodiments where the active ingredient is neramexane mesylate, the active ingredient of the present invention is usually present in amounts ranging from about 2% w/w to about 50% w/w. Preferably, the amounts range from about 2% w/w to about 40% w/w, more preferably from about 3% w/w to about 25% w/w.

In the present invention, the preferred optional pharmaceutically acceptable coating contains hydroxypropyl methylcellulose, such as Opadry® (Colorcon, West Point, Pa.) or Sepifilm® (Seppic, N.J.) present in amounts ranging from about 2% w/w to about 7% w/w, preferably from about 2% w/w to about 5% w/w.

In appropriate embodiments, the formulation contains fillers such as starch and starch derivatives, hydrated sugar alcohols, calcium phosphates, and cellulose based excipients and derivatives thereof.

The oral dosage form of the present invention may further comprise one or more pharmaceutically acceptable carriers, excipients, anti-adherants, stabilizing agents, binders, colorants, disintegrants, glidants, and lubricants.

In another embodiment of the present invention, the dosage forms contain excipients that have improved stability, forming less than 3.0% w/w lactose adduct, preferably less than 2.5% w/w, upon storage for 36 months at room temperature. The present invention discovered the lactose adduct formation, which was not a foreseen adduct formation reaction. One skilled in art will recognize that an adduct, such as a lactose adduct, is formed by a Maillard reaction between the 1-aminocyclohexane analog active ingredient and a lactose excipient.

In one embodiment, the dosage forms contain the filler microcrystalline cellulose, which is present in amounts ranging from about 10% w/w to about 35% w/w, wherein the compositions additionally comprise lactose monohydrate, preferably, from about 18% w/w to about 22% w/w. Such dosage form exhibits less than 3% adduct formation, in 36 months. In alternative embodiments, where no lactose (or any other reducing agent) is present, the microcrystalline cellulose filler is present in amounts ranging from about 20% w/w to about 95% w/w, preferably, in amounts ranging from about 60% w/w to about 90% w/w. Such dosage forms exhibit less than 0.5% adduct formation in 36 months.

In another embodiment of the present invention, the dosage forms contain the lubricant magnesium stearate, which is present in amounts ranging from about 0% to about 2% w/w, preferably, in amounts ranging from about 0.2% to about 0.5% w/w.

In another embodiment, the dosage forms contain an excipient which supports the disintegration of the formulation. This excipient may be starch-based or derivatives thereof, cellulose-based or derivatives thereof, or based on pyrrolidone or a derivative thereof, in amounts ranging from about 0.2 to 10% w/w.

In a preferred embodiment, the composition is in tablet form. The tablet form has a hardness of from about 3 to about 40 Kp. Preferably, the hardness is from about 4 to about 30 Kp. One skilled in art will recognize that hardness of the tablet is also related to shape and size of tablets.

DETAILED DESCRIPTION OF THE INVENTION

Figure 1:
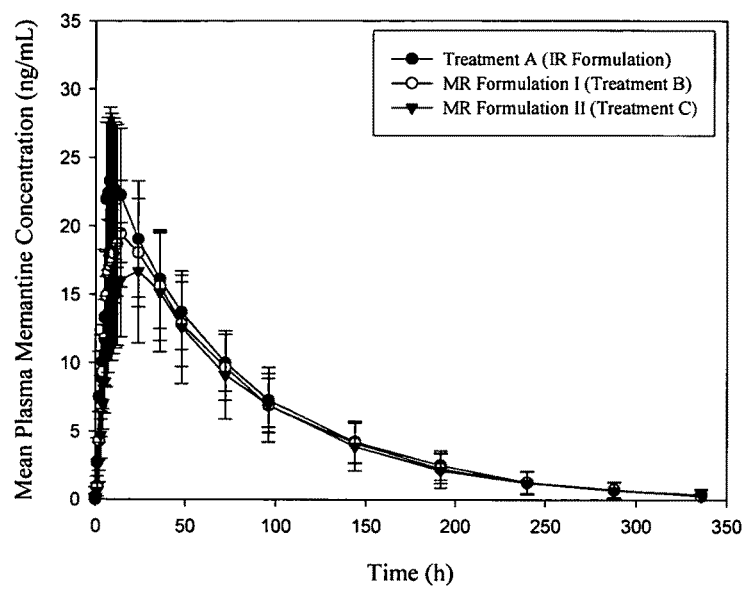
FIG. 1 is a plot of the mean plasma concentrations of memantine (ng/mL) following administration of two-10 mg memantine HCl immediate release tablets of the present invention four hours apart (closed circle) in young healthy male and female subjects over time (hours) elapsed from administration. Also shown in the plots are results of two modified release tablets (open circle and inverted triangle).

In accordance with the present invention, an immediate release pharmaceutical composition is provided for the administration of a 1-aminocyclohexane, preferably memantine or neramexane, and pharmaceutically acceptable salt thereof, to a human or animal subject, where the composition includes oral solid dosage forms, preferably in tablet form.

In the present invention, the pharmaceutical compositions comprise a therapeutically effective amount of a 1-aminocyclohexane, preferably memantine (free base) or neramexane (free base), or a pharmaceutically acceptable salt thereof, preferably the HCl salt and optionally a pharmaceutically acceptable coating, as well as, optionally, one or more carriers, fillers, anti-adherants, excipients, stabilizing agents, binders, colorants, disintegrants, glidants, and lubricants (all pharmaceutically acceptable).

Memantine(1-amino-3,5-dimethyladamantane) and neramexane(1-amino-1,3,3,5,5-pentamethylcyclohexane) can be considered an analog of 1-amino-cyclohexane (disclosed, e.g., in U.S. Pat. Nos. 4,122,193; 4,273,774; 5,061,703), and are systemically-active noncompetitive NMDA receptor antagonists having low to moderate affinity for the receptor and strong voltage dependency and rapid blocking/unblocking kinetics. These pharmacological features allow memantine and neramexane to block sustained activation of the receptor under pathological conditions and to rapidly leave the NMDA channel during normal physiological activation of the channel. Memantine and salts thereof (e.g., the HCl salt, MW 215.77) are indicated for treatment of CNS diseases such as Alzheimer's disease. Memantine has been approved in the United States for the treatment of Alzheimer's Disease and is currently approved outside the United States as an oral formulation for the Alzheimer's Disease and Parkinson's Disease and has been available commercially since 1982. It is currently under investigation for the treatment of neuropathic pain.

The 1-aminocyclohexane compounds of the present invention having NMDA-antagonistic activity can be represented in the general formula (I):

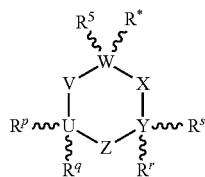

(I)

wherein:
R* is -(A)$_n$-(CR$^1$R$^2$)$_m$—NR$^3$R$^4$,
n and m are integers, and n+m=0, 1, or 2,
A is selected from the group consisting of linear or branched lower alkyl (C$_1$-C$_6$), linear or branched lower alkenyl (C$_2$-C$_6$), and linear or branched lower alkynyl (C$_2$-C$_6$);

R$^1$ and R$^2$ are independently selected from the group consisting of hydrogen, linear or branched lower alkyl (C$_1$-C$_6$), linear or branched lower alkenyl (C$_2$-C$_6$), linear or branched lower alkynyl (C$_2$-C$_6$) aryl, substituted aryl and arylalkyl;

R$^3$ and R$^4$ are independently selected from the group consisting of hydrogen, linear or branched lower alkyl (C$_1$-C$_6$), linear or branched lower alkenyl (C$_2$-C$_6$), and linear or branched lower alkynyl (C$_2$-C$_6$), or together form alkylene (C$_2$-C$_{10}$) or alkenylene (C$_2$-C$_{10}$) or together with the N form a 3-7-membered azacycloalkane or azacycloalkene, including a substituted (alkyl (C$_1$-C$_6$), alkenyl (C$_2$-C$_6$)) 3-7-membered azacycloalkane or azacycloalkene; or independently R$^3$ or R$^4$ may join with R$^p$, R$_q$, R$^r$, or R$^s$ to form an alkylene chain —CH(R$^6$)—(CH$_2$)$_t$—, wherein t=0 or 1 and the left side of the alkylene chain is attached to U or Y and the right side of the alkylene chain is attached to N and R$^6$ is selected from the group consisting of hydrogen, linear or branched lower alkyl (C$_1$-C$_6$), linear or branched lower alkenyl (C$_2$-C$_6$), linear or branched lower alkynyl (C$_2$-C$_6$), aryl, substituted aryl and arylalkyl; or independently R$^3$ or R$^4$ may join with R$^5$ to form an alkylene chain represented by the formula —CH$_2$—CH$_2$—CH$_2$—(CH$_2$)$_t$—, or an alkenylene chain represented by the formulae —CH=CH—CH$_2$—(CH$_2$)$_t$—, —CH=C=CH—(CH$_2$)$_t$— or —CH$_2$—CH=CH—(CH$_2$)$_t$—, wherein t=0 or 1, and the left side of the alkylene or alkenylene chain is attached to W and the right side of the alkylene ring is attached to N;

R$^5$ is independently selected from the group consisting of hydrogen, linear or branched lower alkyl (C$_1$-C$_6$), linear or branched lower alkenyl (C$_2$-C$_6$), and linear or branched lower alkynyl (C$_2$-C$_6$), or R$^5$ combines with the carbon to which it is attached and the next adjacent ring carbon to form a double bond;

R$^p$, R$^q$, R$^r$, and R$^s$, are independently selected from the group consisting of hydrogen, linear or branched lower alkyl (C$_1$-C$_6$), linear or branched lower alkenyl (C$_2$-C$_6$), linear or branched lower alkynyl (C$_2$-C$_6$), cycloalkyl (C$_3$-C$_6$) and aryl, substituted aryl and arylalkyl or R$^p$, R$^q$, R$^r$, and R$^s$ independently may form a double bond with U or with Y or to which it is attached, or R$^p$, R$^q$, R$^r$, and R$^s$ may combine together to represent a lower alkylene —(CH$_2$)$_x$— or a lower alkenylene bridge wherein x is 2-5, inclusive, which alkylene bridge may, in turn, combine with R$^5$ to form an additional lower alkylene —(CH$_2$)$_y$— or a lower alkenylene bridge, wherein y is 1-3, inclusive; and the ring defined by U—V—W—X—Y—Z represents an optionally unsaturated cyclohexane ring wherein U, W, and Y represent carbon atoms and V, X, and Z each independently represent a carbon atom, CH, or CH$_2$, (or the definitions of U, W, Y on one hand and V, X, and Z can be reversed including corresponding placement of the R groups R*, R$^5$, R$^p$, R$^q$, R$^r$, and R$^s$), it being understood that the valence requirements of the ring atoms are respected, and include optical isomers, diastereomers, polymorphs, enantiomers, hydrates, pharmaceutically acceptable salts, and mixtures of compounds within formula (I).

The ring defined by U—V—W—X—Y—Z is preferably selected from the group consisting of cyclohexane, cyclohex-2-ene, cyclohex-3-ene, cyclohex-1,4-diene, cyclohex-1,5-diene, cyclohex-2,4-diene, and cyclohex-2,5-diene.

Compounds of Formula I may be adamantyl substances.

Non-limiting examples of 1-aminocyclohexane compounds used according to the invention include the 1-aminoalkylcyclohexane derivatives selected from the group consisting of:
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane(neramexane),
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane,
N-(1,3,3,5,5-pentamethylcyclohexyl)pyrrolidine,
3,3,5,5-tetramethylcyclohexylmethylamine,
1-amino-1-propyl-3,3,5,5-tetramethylcyclohexane,
1 amino-1,3,3,5(trans)-tetramethylcyclohexane (axial amino group
3-propyl-1,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-1(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5,5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl-1)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis),5(cis)-trimethylcyclohexane,
1-amino-(1R,SS)trans-5-ethyl-1,3,3-trimethylcyclohexane,
1-amino-(1S,SS)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,SS)cis-5-ethyl-1,3,3-trimethylcyclohexyl]pyrrolidine or piperidine,
N-(1,3,3-trimethyl-trans-5-ethylcyclohexyl)pyrrolidine or piperidine,
N-[(1R,SS)trans-5-ethyl,3,3-trimethylcyclohexyl]pyrrolidine or piperidine,
N-(1-ethyl-3,3,5,5-tetramethylyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine,
their optical isomers, diastereomers, enantiomers, hydrates, their pharmaceutically acceptable salts, and mixtures thereof.

Neramexane(1-amino-1,3,3,5,5-pentamethylcyclohexane) is disclosed, e.g., U.S. Pat. No. 6,034,134, which is incorporated herein by reference in its entirety.

Certain 1-aminocyclohexane derivatives of general formula (I) including the case where three axial alkyl substituent, e.g., $R^p$, $R^r$ and $R^5$ all together form a bridgehead to yield compounds (so called 1-aminoadamantanes) illustrated by the formulae IIb and IId below:

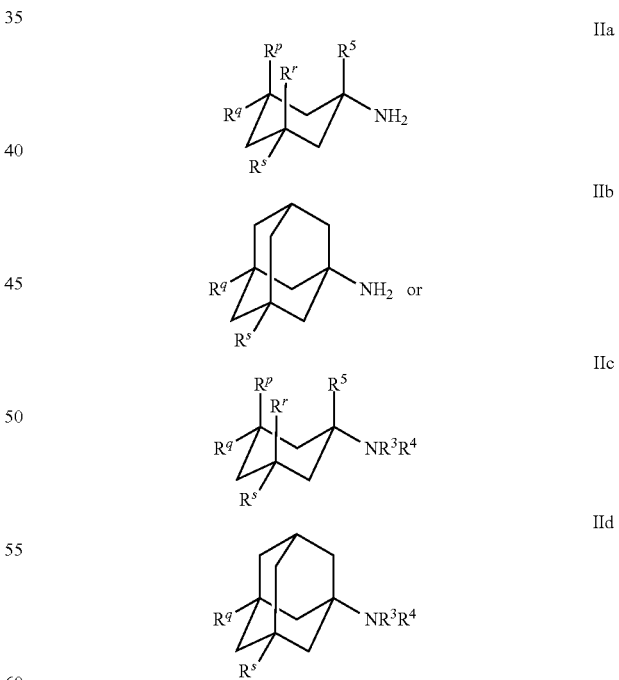

Certain 1-aminocyclohexane derivatives of formula (I) wherein n+m=0, U, V, W, X, Y and Z form a cyclohexane ring, and one or both of $R^3$ and $R^4$ are independently joined to said cyclohexane ring via alkylene bridges formed through $R^p$, $R^q$, $R^r$, $R^s$ or $R^5$ are represented by the following formulae IIIa-IIIc:

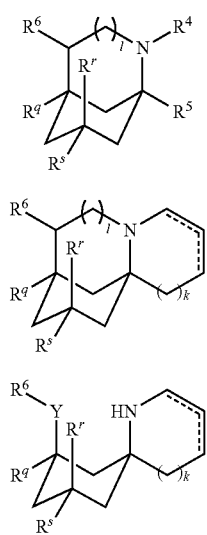

wherein $R^q$, $R^r$, $R^s$, $R^r$ and $R^5$ are as defined above for formula (I), $R^6$ is hydrogen, linear or branched lower alkyl ($C_1$-$C_6$), linear or branched lower alkenyl ($C_2$-$C_6$), linear or branched lower alkynyl ($C_2$-$C_6$), aryl, substituted aryl or arylalkyl, Y is saturated or may combine with $R^6$ to form a carbon-hydrogen bond with the ring carbon to which it is attached, l=0 or 1 and k=0, 1 or 2 and represents a single or double bond.

Non-limiting examples of 1-aminocyclohexane compounds used according to the invention include 1-amino adamantane and its derivatives selected from the group consisting of:
1-amino-3-phenyl adamantane,
1-amino-methyl adamantane,
1-amino-3,5-dimethyl adamantane(memantine),
1-amino-3-ethyl adamantane,
1-amino-3-isopropyl adamantane,
1-amino-3-n-butyl adamantane,
1-amino-3,5-diethyl adamantane,
1-amino-3,5-diisopropyl adamantane,
1-amino-3,5-di-n-butyl adamantane,
1-amino-3-methyl-5-ethyl adamantane,
1-N-methylamino-3,5-dimethyl adamantane,
1-N-ethylamino-3,5-dimethyl adamantane,
1-N-isopropyl-amino-3,5-dimethyl adamantane,
1-N,N-dimethyl-amino-3,5-dimethyl adamantane,
1-N-methyl-N-isopropyl-amino-3-methyl-5-ethyl adamantane,
1-amino-3-butyl-5-phenyl adamantane,
1-amino-3-pentyl adamantane,
1-amino-3,5-dipentyl adamantane,
1-amino-3-pentyl-5-hexyl adamantane,
1-amino-3-pentyl-5-cyclohexyl adamantane,
1-amino-3-pentyl-5-phenyl adamantane,
1-amino-3-hexyl adamantane,
1-amino-3,5-dihexyl adamantane,
1-amino-3-hexyl-5-cyclohexyl adamantane,
1-amino-3-hexyl-5-phenyl adamantane,
1-amino-3-cyclohexyl adamantane,
1-amino-3,5-dicyclohexyl adamantane,
1-amino-3-cyclohexyl-5-phenyl adamantane,
1-amino-3,5-diphenyl adamantane,
1-amino-3,5,7-trimethyl adamantane,
1-amino-3,5-dimethyl-7-ethyl adamantane,
1-amino-3,5-diethyl-7-methyl adamantane,
1-N-pyrrolidino and 1-N-piperidine derivatives,
1-amino-3-methyl-5-propyl adamantane,
1-amino-3-methyl-5-butyl adamantane,
1-amino-3-methyl-5-pentyl adamantane,
1-amino-3-methyl-5-hexyl adamantane,
1-amino-3-methyl-5-cyclohexyl adamantane,
1-amino-3-methyl-5-phenyl adamantane,
1-amino-3-ethyl-5-propyl adamantane,
1-amino-3-ethyl-5-butyl adamantane,
1-amino-3-ethyl-5-pentyl adamantane,
1-amino-3-ethyl-5-hexyl adamantane,
1-amino-3-ethyl-5-cyclohexyl adamantane,
1-amino-3-ethyl-5-phenyl adamantane,
1-amino-3-propyl-5-butyl adamantane,
1-amino-3-propyl-5-pentyl adamantane,
1-amino-3-propyl-5-hexyl adamantane,
1-amino-3-propyl-5-cyclohexyl adamantane,
1-amino-3-propyl-5-phenyl adamantane,
1-amino-3-butyl-5-pentyl adamantane,
1-amino-3-butyl-5-hexyl adamantane,
1-amino-3-butyl-5-cyclohexyl adamantane,
their optical isomers, diastereomers, enantiomers, hydrates, N-methyl, N,N-dimethyl, N-ethyl, N-propyl derivatives, their pharmaceutically acceptable salts, and mixtures thereof.

Memantine(1-amino-3,5-dimethyl adamantane), for example, is the subject matter of U.S. Pat. Nos. 4,122,193 and 4,273,774, both incorporated herein by reference in their entirety. Neramexane, for example, is the subject matter of U.S. Pat. No. 6,034,134, incorporated herein by reference in its entirety.

The 1-amino adamantane compounds of formulae IIb and IId, including memantine, are generally prepared by alkylation of halogenated adamantanes, preferably bromo- or chloroadamantanes. The di- or tri-substituted adamantanes are obtained by additional halogenation and alkylation procedures. The amino group is introduced either by oxidation with chromiumtrioxide and bromination with HBr or bromination with bromine and reaction with formamide followed by hydrolysis. The amino function can be alkylated according to generally-accepted methods. Methylation can, for example, be effected by reaction with chloromethyl formate and subsequent reduction. The ethyl group can be introduced by reduction of the respective acetamide. For more details on synthesis see, e.g., U.S. Pat. Nos. 5,061,703 and 6,034,134. Additional synthetic techniques for the foregoing compounds can be found in published U.S. Application Nos. 2003/0166634 and 2004/0034055, all incorporated by reference in their entirety.

According to the invention, the 1-aminocyclohexane derivatives of formula (I) may be applied as such or used in the form of their pharmaceutically acceptable salts. Suitable salts of the compound include, but are not limited to, acid addition salts, such as those made with hydrochloric, methylsulfonic, hydrobromic, hydroiodic, perchloric, sulfuric, nitric, phosphoric, acetic, propionic, glycolic, lactic pyruvic, malonic, succinic, maleic, fumaric, maleic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin. In a preferred embodiment, the salt is memantine hydrochloride ($C_{12}H_{21}N.HCl$, MW 215.77). In another preferred embodiment, the salt is neramexane mesylate ($C_{11}H_{23}N.CH_4O_3S$, MW 265.42). The term "salts" can also include addition salts of free acids. All of these salts (or other similar salts) may be prepared by conventional means.

All such salts are acceptable provided that they are non-toxic and do not substantially interfere with the desired pharmacological activity.

The present invention further includes all individual enantiomers, diastereomers, racemates, and other isomers of those compounds wherein such structural variations are possible. The invention also includes all polymorphs and solvates, such as hydrates and those formed with organic solvents, of these compounds. Such isomers, polymorphs, and solvates may be prepared by methods known in the art, such as by crystallization from different solvents, or by regiospecific and/or enantioselective synthesis and resolution, based on the disclosure provided herein.

The present invention includes derivatives of the compound of the present invention. Examples of derivatives applicable to the invention include, but are not limited to, structurally related compounds composed of a tricyclic 10-carbon ring bearing an amino group such as nitroxy-memantine derivatives (such as nitroprusside, nitroglycerin, or an NO-generating derivative of nitroprusside or nitroglycerin in U.S. Pat. Nos. 5,234,956 and 5,455,279).

In one preferred embodiment, the active ingredient is memantine hydrochloride. The active ingredient is present in amounts ranging broadly from about 2.5 mg to about 80 mg, preferably ranging from about 5 mg to about 60 mg. In a preferred embodiment, compositions contain between about 2% and about 20% w/w memantine; preferably from about 3.2% to about 10% w/w memantine; most preferably from about 3.9% to about 8.4% w/w memantine.

In another preferred embodiment, the active ingredient is neramexane mesylate. The active ingredient is present in amounts ranging broadly from about 6.25 mg to about 150 mg, preferably ranging from about 12.5 mg to about 125 mg. The active ingredient, e.g., neramexane mesylate in the oral dosage form of the present invention is usually present in amounts ranging from about 2% w/w to about 50% w/w. Preferably, the amounts range from about 2% w/w to about 40% w/w, more preferably from about 3% w/w to about 25% w/w.

The immediate-release dosage form optionally has a coating applied or deposited over the entire surface of a unitary release core. Immediate release of the drug is achieved by any of various methods known in the art including the use of a very thin layer or coating, which by virtue of its thinness (i.e., less than about 100 micron) is quickly penetrated by gastric fluid allowing fast leaching of the drug.

In the present invention, examples of coating materials that rapidly disintegrate and disperse include lactose and microcrystalline cellulose, colloidal silicon dioxide, hydrophilic polymers such as hydroxypropyl methylcellulose, PVA, methacrylates (e.g., Eudragit® Rohm Pharma Polymer, Piscataway, N.J.) natural polymers such as xanthan gum, and combinations thereof (e.g., Prosolv®, which contains microcrystalline cellulose and colloidal silicone dioxide). In formulations with a lactose free environment, colloidal silicon dioxide may be necessary in addition to the use of microcrystalline cellulose, e.g., Avicel®. These materials may also be present as excipients in addition to common auxiliary agents and additives or fillers including tabletting aids, colorants, binders, fillers, glidants, and lubricants (all pharmaceutically acceptable).

In one preferred embodiment of the invention, hydroxypropyl methylcellulose is used as a coating material. The optional coating material is present in amounts ranging from about 1 mg to about 70 mg, preferably from about 3 mg to about 60 mg, more preferably from about 3 mg to about 40 mg. In a preferred embodiment, compositions contain from about 2% w/w to about 5% w/w coating material containing hydroxypropyl methylcellulose; more preferably from about 2% to about 4% w/w coating material containing hydroxypropyl methylcellulose.

Fillers or disintegrants act to modify the dissolution pattern. Examples of such fillers include lactose monohydrate, microcrystalline cellulose, Prosolv®, hydroxypropyl methylcellulose, and combinations thereof. Lactose monohydrate, when used, counterbalances the less soluble ingredients of the composition, thereby acting as a disintengrant, whereas microcrystalline cellulose and similar type filler when employed in a lactose-free environment may require additional disintegrants such as croscarmellose sodium. Disintegrants in the dosage forms may further contain an excipient to support the disintegration of the formulation. One skilled in art recognizes that these excipients may be starch based, cellulose based or pyrrolidone based, or a derivative thereof, in amounts ranging from about 0.2 to 10%.

When hydroxypropyl methylcellulose or ethyl cellulose are used in a matrix tablet, the dissolution rates are much lower than the immediate release rate targeted. This is because the hydrophobic matrix tablets that result when these polymers release the drug by mechanism of polymer erosion. Since the erosion from a hydrophobic matrix is very slow, the dissolution rate of the readily soluble active ingredient is also slow.

In one embodiment of the present invention in formulation containing memantine, lactose monohydrate is used as a filler. Lactose monohydrate is present in amounts ranging from about 40 mg to about 1,400 mg, preferably from about 80 mg to about 1,050 mg. In another embodiment, the compositions contain from about 50% to about 80% w/w lactose monohydrate, preferably from about 60% w/w to about 75% w/w. Lactose adduct formation is less than 3% w/w, more preferably less than 2.5% w/w.

In a preferred embodiment of the invention containing memantine, microcrystalline cellulose (MCC) is used as a filler. In formulations containing lactose monohydrate, MCC is used as an additional filler, present in amounts ranging from about 13 mg to about 420 mg, preferably from about 25 to about 315 mg per unit dose. In one embodiment, the MCC is present in amounts from about 10% w/w to about 35% w/w, preferably from about 18% w/w to about 22% w/w.

If the MCC is used as a filler in the absence of lactose monohydrate, the MCC is present in an amount ranging from about 50 mg to about 1,600 mg, preferably from about 100 mg to about 1,200 mg per unit dose. In a preferred embodiment, compositions contain from about 20% w/w to about 95% w/w microcrystalline cellulose; more preferably from about 60% w/w to about 90% w/w. The microcrystalline cellulose provides the desired dissolution profiles with acceptable or improved formulation and processing properties. One skilled in art will recognize that these microcrystalline cellulose based formulations contain disintegrants. Disintgrants are starch-based, cellulose-based or pyrrolidone-based excipients, or based on a derivative of any of the foregoing, in amounts ranging from about 0.2 to 10% w/w.

Additional excipients such as talc (an anti-adherant), starch, dicalcium phosphate, mannitol, croscarmellose sodium, colloidal silicon dioxide, sodium starch glycolate can also be used in combination. Use of the disinetgrants or soluble fillers allow for rapid disintegration of tablets exposing large surface area and the drug leading to faster dissolution of the drug.

Additionally, the dosage forms contain excipients that form less than 3.0% adduct, preferably less than 2.5%, even 0% in lactose-free formulations. One skilled in art will recognize that substances such as memantine and neramexane adducts result from a Maillad reaction. Adducts, such as the lactose or other reducing sugar adducts, may form with the amines in adamantane derivatives.

Tablets in accordance with this invention can be prepared by conventional mixing, comminution, and tabletting techniques that are well-known in the pharmaceutical formulations industry. The immediate-release tablet, for example, may be fabricated by direct compression by punches and dies fitted to a rotary tabletting press, ejection or compression molding, granulation followed by compression, or forming a paste and extruding the paste into a mold or cutting the extrudate into short lengths followed by compression. As mentioned above, the immediate release component may be applied as a coating over the core by spraying, dipping, or pan-coating, or as an additional layer by tabletting or compression. Preferably, the process used for preparing tablets is direct compression of the blend. Ordinarily, direct blending is a difficult process, and problems such as blend segregation, low compressibility and low content uniformity can occur. However, neither the formulations described in this invention nor the process for making them exhibit these problems, or such problems are substantially less significant. Near IR spectroscopic methods showed good distribution of the drug in the tablets.

When tablets are made by direct compression, the addition of lubricants may be helpful and is sometimes important to promote powder flow and to prevent "capping" of the tablet (the breaking off of a portion of the tablet) when the pressure is relieved. Useful lubricants are magnesium stearate and hydrogenated vegetable oil (preferably hydrogenated and refined triglycerides of stearic and palmitic acids). In a preferred embodiment, magnesium stearate is used as a lubricant in an amount from about 0 mg to about 6 mg, preferably from about 0.3 mg to about 4.0 mg. In a preferred embodiment, the compositions contain from about 0% w/w to about 2% w/w magnesium stearate; more preferably from about 0.2% w/w to about 0.5% w/w magnesium stearate. Additional excipients may be added to enhance tablet hardness, powder flowability, and to reduce tablet friability and adherence to the die wall.

Tablet hardness is linearly affected by different compression forces, shape and size of the tablet. As compression forces increase (kN), there is a linear increase in tablet hardness (Kp). Preferably, hardness values range from about 3 to about 40 Kp, more preferably from about 4 to about 30 Kp. In addition, at lower compression, and thus lower hardness values, e.g., lower than 3 Kp, the logo and product identification de-bossing was "picked" making it difficult to read and aesthetically less pleasing. At the higher compression and hardness values, the picking was eliminated without affecting dissolution at 30 minutes (see Example 1).

The plasma concentration of the dose proportional immediate release memantine formulations have a time of maximum plasma concentration ($T_{max}$) in human patients ranging from between about 3 to about 7 hours, more often averaging between about 4 to about 6 hours, and an in vitro release rate of more than about 80% in about 60 minutes, more preferably in about 30 minutes.

The plasma concentration of the dose proportional immediate release formulations of neramexane have a time of maximum plasma concentration ($T_{max}$) ranging from between about 2 to about 8 hours, more often averaging between about 2 to about 7 hours, and an in vitro release rate of more than about 80% in about 60 minutes, more preferably in about 30 minutes.

The pharmaceutical formulations of the present invention allow for dose-proportional compositions and the modification of the $C_{max}$ by changing the strength of the formulation without substantially affecting the $T_{max}$ of the drug. The 30-minute immediate release formulations described in the present invention provide the desired $T_{max}$ without compromising the initial peak ($C_{max}$), which is characteristic of memantine or neramexane salts.

In addition, a long $T_{1/2}$ allows for either twice a day, or preferably once a day, administration for an immediate release dosage form and achieves a relatively high $C_{max}$ which is considered essential for the pharmacological efficacy of the product. For example, the $C_{max}$ for 20 mg memantine (administered at two 10 mg tablets 4 hours apart) would fall within the range of about 15 to about 40 ng/ml, with an average value of about 25 ng/ml. If the memantine or neramexane dosage form is administered twice a day, administrations being approximately 4 hours apart, the average $T_{max}$ is about 8 hours±2 hours. In addition, the dose proportionality allows up-titration beginning with lower doses for patient using an essentially identical formulation composition and varying essentially only the weight content of memantine or neramexane to achieve different strengths.

In accordance with the present invention, an immediate release pharmaceutical composition is provided for the once daily administration or, if preferred, twice per day, of memantine or a pharmaceutically acceptable salt thereof, preferably its HCl salt, to a human or animal subject. In accordance with the present invention, an immediate release pharmaceutical composition is provided for the once daily administration or, if preferred, twice per day, of neramexane or a pharmaceutically acceptable salt thereof, preferably its mesylate salt, to a human or animal subject.

In an alternative embodiment of the invention, the rapid dissolution profile of the tablets enables drinkable solutions for patients unable to ingest tablets.

The memantine and neramexane formulations of the invention are suitable for the treatment of CNS diseases, including but not limited to the treatment of Alzheimer's disease, Parkinson's disease, AIDS dementia (U.S. Pat. No. 5,506,231, see also Parsons et al., Neuropharmacology 1999 June; 38(6): 735-67), neuropathic pain (U.S. Pat. No. 5,334,618), cerebral ischemia, epilepsy, glaucoma, hepatic encephalopathy, multiple sclerosis, stroke, depression (U.S. Pat. No. 6,479,553), tardive dyskinesia, malaria, Borna virus, Hepatitis C (U.S. Pat. Nos. 6,034,134 and 6,071,966). Additional pathologies for treatment of which memantine is suitable are disclosed in U.S. Pat. Nos. 5,614,560 and 6,444,702. Accordingly, the present invention further provides a method for the therapeutic or prophylactic treatment of CNS disorders in a human or animal subject, the method including administering to the subject a composition in accordance with the present invention.

As used herein, "adduct formation" refers to the formation of a compound with a particular formulation of a composition by a solid phase reaction. The general term "adduct" for a compound, also called an addition compound, results from the direct combination of two or more different compounds. For example, in the present invention, lactose adduct formation may occur with formulations containing lactose. Such adduct formation detracts from the efficacy of the product and increases the risks of other side effects.

As used herein, a "therapeutically effective amount" means the amount of a compound that, when administered to a mammal for treating a state, disorder or condition is sufficient to effect such treatment. The "therapeutically effective amount" will vary depending on the compound, the disease and its severity and the age, weight, physical condition and responsiveness of the mammal to be treated. According to the present invention, in one embodiment, a therapeutically effective amount of memantine is an amount effective to treat CNS disorders, including Alzheimer's disease or Parkinson's disease. Other uses include, but are not limited to, the treatment of dementia and depression. The effective amount of the drug for pharmacological action, and therefore the tablet strength, depends on the disease itself, e.g., in Alzheimer's disease, the patient is initially given a 5 mg dose and the dosage is progressively increased to 10 mg twice a day to 20 mg once a day. Similar up-titrations but starting from higher base amounts (e.g., base values starting at about 12 to about 15 mg, titrating up to about 80 mg) are useful for pain relief, e.g., neuropathic pain. Such titration may be facilitated by providing a selection of tablets representing standard or common, doses, for example, 5 mg, 10 mg, 15 mg, 20 mg, 40 mg and 80 mg doses of active substance. Therefore, it is important to have a dose proportional formulation.

As used herein, the term "pharmaceutically acceptable" refers to biologically or pharmacologically compatible for in vivo use, and preferably means approved by a regulatory agency of the Federal or a state government or listed in the U.S. Pharmacopeia or other generally recognized pharmacopeia for use in animals, and more particularly in humans.

As used herein, the term "treat" and its derivatives are used herein to mean to relieve or alleviate pain in a hypersensitive mammal or in a mammal suffering from a CNS disorder, e.g., dementia or Parkinson's disease. The term "treat" may mean to relieve or alleviate the intensity and/or duration of a manifestation of disease experienced by a subject in response to a given stimulus (e.g., pressure, tissue injury, cold temperature, etc.). For example, in relation to dementia, the term "treat" may mean to relieve or alleviate cognitive impairment (such as impairment of memory and/or orientation) or impairment of global functioning (activities of daily living, ADL) and/or slow down or reverse the progressive deterioration in ADL or cognitive impairment. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject. Within the meaning of the present invention, the dementia is associated with a CNS disorder, including without limitation neurodegenerative diseases such as Alzheimer's disease (AD).

The term "picking" refers to the detachment of material (such as a film fragment) from the surface of a tablet upon contact with another object and its adherence to the surface of the other object (such as another tablet or a tooling) (See Pharmaceutical Dosage Forms: Tablets Volume 3, edited by H. A. Lieberman and L. Lachman, pp. 101 and 272 (Marcel Dekker, Inc. 1982)). Picking may occur, for example, when tablets are compressed or tumbled. The material removed may obscure or obliterate logos, monograms, lettering, and numbering which were intended to appear on the surface of the tablet.

The term "dose proportional" as used herein refers to the relationship between the dose of a drug and its bioavailability. For example, in the present invention, twice as much of the same composition to make a dosage form that will deliver twice the drug will provide the same bioavailability (i.e., AUC and $C_{max}$) as one dose of the dosage form. The dose proportionality of the present invention applies to a wide range of doses as discussed in detail herein.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value. For example, when referring to a period of time, e.g., hours, the present values (±20%) are more applicable. Thus, 6 hours can be, e.g., 4.8 hours, 5.5 hours, 6.5 hours, 7.2 hours, as well as the usual 6 hours.

The term "use environment" when applied to the formulations means the gastric fluids of a patient to whom the formulation is administered or simulated dissolution media.

EXAMPLES

The present invention will be better understood by reference to the following Examples, which are provided as exemplary of the invention, and not by way of limitation.

Example 1

Preparation of Memantine HCl Immediate Release Tablets

The present example describes the process of developing memantine hydrochloride immediate release tablets in 2.5, 5, 10, 15, 20, 40, 60, and 80 mg dosages.

Materials and Methods

The following tables provide the makeup of immediate release tablets including the active components, coating agent, and other excipients for the specified dosage forms with specific target release time periods. Tables 1 and 2 provide the makeup of tablets with lactose and contain the same data expressed respectively in absolute (mg) or relative (% w/w) terms.

TABLE 1

2.5 mg to 80 mg Dose Proportional Formulations (with lactose/MCC)

| Component or ingredient (mg) | Content (mg) | | | | | | | |
| --- | --- | --- | --- | --- | --- | --- | --- | --- |
| Memantine HCl | 2.5 | 5 | 10 | 15 | 20 | 40 | 60 | 80 |
| Microcrystalline Cellulose | 13.03 | 26.05 | 52.10 | 78.15 | 104.20 | 208.40 | 312.60 | 416.8 |
| Lactose Monohydrate | 43.69 | 87.38 | 174.75 | 262.13 | 349.50 | 699.00 | 1048.50 | 1398.0 |
| Colloidal Silicone Dioxide | 0.32 | 0.63 | 1.25 | 1.88 | 2.50 | 5.00 | 7.50 | 10.0 |

TABLE 1-continued

2.5 mg to 80 mg Dose Proportional Formulations (with lactose/MCC)

| Component or ingredient (mg) | Content (mg) | | | | | | | |
|---|---|---|---|---|---|---|---|---|
| Talc | 2.79 | 5.57 | 11.15 | 16.72 | 22.30 | 44.60 | 66.90 | 89.2 |
| Magnesium Stearate | 0.19 | 0.37 | 0.75 | 1.12 | 1.50 | 3.00 | 4.50 | 6.0 |
| Weight of Uncoated Tablet | 62.52 | 125.00 | 250.00 | 375.00 | 500.00 | 1000.00 | 1500.00 | 2000.0 |
| Coating Opadry, (containing hydroxypropyl methylcellulose) | 1.88 | 3.75 | 7.50 | 11.25 | 15.00 | 30.00 | 45.00 | 60.0 |
| Total Coated Tablet | 64.40 mg | 128.75 mg | 257.50 mg | 386.25 mg | 515.00 mg | 1030.00 mg | 1545.00 mg | 2060.00 mg |

For the dose proportional formulations of Table 1, the percentage w/w for each of the active ingredient and excipients are identified in Table 2.

TABLE 2

| Weights in % w/w of tablet (lactose/MCC) | |
|---|---|
| Component or ingredient | All Strengths |
| Memantine HCl | 3.9 |
| Microcrystalline Cellulose | 20.2 |
| Lactose Monohydrate | 67.8 |
| Colloidal Silicone Dioxide | 0.5 |
| Talc | 4.3 |
| Magnesium Stearate | 0.3 |
| Coating Opadry (Contains hydroxypropyl methylcellulose) | 2.9 |
| Total | 100.0 |

Tables 3a-3c and Table 4 also provide the makeup of tablets without lactose and contain the same data expressed respectively in absolute (mg) or relative (% w/w) terms.

TABLE 3a

2.5 mg to 80 mg Dose Proportional Formulations (lactose free)
Composition in mg per Tablet

| Component or ingredient | 2.5 mg | 5 mg | 10 mg | 15 mg | 20 mg | 40 mg | 60 mg | 80 mg |
|---|---|---|---|---|---|---|---|---|
| Memantine HCl | 2.5 | 5.0 | 10.0 | 15.0 | 20.0 | 40.0 | 60.0 | 80.0 |
| Microcrystalline Cellulose (Prosolv ®)* | 48.8 | 97.5 | 195.0 | 292.5 | 390.0 | 780.0 | 1170.0 | 1560.0 |
| Croscarmellose Sodium | 1.1 | 2.2 | 4.4 | 6.6 | 8.8 | 17.6 | 26.4 | 35.2 |
| Talc | 2.5 | 5.0 | 10.0 | 15.0 | 20.0 | 40.0 | 60.0 | 80.0 |
| Mg stearate | 0.2 | 0.3 | 0.6 | 0.9 | 1.2 | 2.4 | 3.6 | 4.8 |
| Total Core Tablet* | 55.0 | 110.0 | 220.0 | 330.0 | 440.0 | 880.0 | 1320.0 | 1760.0 |
| Coating Opadry ® (Containing HPMC) | 1.7 | 3.3 | 6.6 | 9.9 | 13.2 | 26.4 | 39.6 | 52.8 |
| Total coated | 56.7 | 113.3 | 226.6 | 339.9 | 453.2 | 906.4 | 1359.6 | 1812.8 |

*Core weight may be adjusted with fillers to +/−10% depending on filler densities.
Prosolv ® is a mixture of microcrystalline cellulose and colloidal silicone dioxide

TABLE 3b

6.25 mg to 125 mg Dose Proportional Formulations (lactose free)
Exact formula composition (Composition in mg per Tablet)

| Excipient | 6.25 mg | 12.5 mg | 25 mg | 37.5 mg | 50 mg | 75 mg | 100 mg | 125 mg |
|---|---|---|---|---|---|---|---|---|
| Neramexane Mesylate | 6.25 | 12.5 | 25.0 | 37.5 | 50.0 | 75.0 | 100.0 | 125.0 |
| Microcrystalline Cellulose (Avicel ® or ProSolv ®)* | 51.6 | 103.2 | 206.5 | 309.7 | 413.0 | 619.5 | 826.0 | 1032.5 |
| Colloidal Silicon Dioxide | 0.6 | 1.3 | 2.5 | 3.8 | 5.0 | 7.5 | 10.0 | 12.5 |
| Croscarmellose Sodium | 3.1 | 6.3 | 12.5 | 18.8 | 25.0 | 37.5 | 50.0 | 62.5 |
| Talc | 0.6 | 1.3 | 2.5 | 3.8 | 5.0 | 7.5 | 10.0 | 12.5 |
| Magnesium Stearate | 0.2 | 0.5 | 1.0 | 1.5 | 2.0 | 3.0 | 4.0 | 5.0 |
| Total core tablet* | 62.5 | 125.0 | 250.0 | 375.0 | 500.0 | 750.0 | 1000.0 | 1250.0 |
| Coating (HPMC), Opadry or Sepifilm | 2.5 | 5.0 | 10.0 | 15.0 | 20.0 | 30.0 | 40.0 | 50.0 |
| Total coated | 65 | 130 | 260 | 390 | 520 | 780 | 1040 | 1300 |

*Core weight may be adjusted with fillers to +/−10% depending on filler density.

TABLE 3c 10 mg to 80 mg Dose Proportional Formulations for Memantine Tablets, 10 mg to 80 mg (lactose free) High Drug Load with Smaller Tablet Size Composition in mg per Tablet

| Excipient | 10 mg | 20 mg | 40 mg | 60 mg | 80 mg |
|---|---|---|---|---|---|
| Memantine HCl | 10.0 | 20.0 | 40.0 | 60.0 | 80.0 |
| Microcrystalline Cellulose (ProSolv or Avicel)* | 31.7 | 63.4 | 126.9 | 190.3 | 253.7 |
| Colloidal Silicon Dioxide** | 0.2 | 0.5 | 0.9 | 1.4 | 1.8 |
| Croscarmellose Sodium | 0.9 | 1.8 | 3.6 | 5.4 | 7.2 |
| Talc | 2.0 | 4.1 | 8.1 | 12.2 | 16.2 |
| Magnesium Stearate | 0.1 | 0.3 | 0.5 | 0.8 | 1.1 |
| Total core tablet* | 45 | 90 | 180 | 270 | 360 |
| Coating (HPMC) Opadry | 1.5 | 3.0 | 6 | 9 | 12 |
| Total coated | 46.5 | 93.0 | 186 | 280 | 372 |

*Core weight may be adjusted with fillers to +/−10% depending on filler density.
**Colloidal silicon dioxide may not be used.

For the dose proportional formulations of Table 3c, the percentage w/w for each of the active ingredient and excipients are identified in Table 4.

TABLE 4

Weights in % w/w of tablet (lactose free) all strengths, including high drug load

| Excipient | Memantine Tablets (2.5 mg to 80 mg) | Neramexane Tablets (6.25-150 mg) |
|---|---|---|
| Memantine Hydrochloride | 4.4-21.6 | 0 |
| Neramexane Mesylate | 0 | 9.6 |
| Microcrystalline Cellulose (Prosolv ®, or Avicel ® plus Colloidal Silicon Dioxide) | 68.4-85.6 | 79.4 |
| Colloidal Silicon Dioxide | — (Prosolv ®) | 1.0 (Avicel ®) |
| Croscarmellose Sodium | 1.9 | 4.8 |
| Talc | 4.4 | 1.0 |
| Magnesium Stearate | 0.3 | 0.4 |
| Coating (HPMC), Opadry or Sepifilm | 2.9 | 3.8 |
| Total | 100.0% | 100.0% |

Test batches of each of the tablets were prepared according to the process outlined below.

Preparation of Blend for Tabletting (lactose/MCC). Approximately half of the amount of microcrystalline cellulose and active drug was placed into a 20 ft$^3$ cone blender. Colloidal silicon dioxide was screened with the remainder of the microcrystalline cellulose through about 0.71 mm screen and added to the 20 ft$^3$ cone blender. The components were mixed for 6 minutes with the intensifier bar off. The lactose monohydrate (when called in the formula) and talc were screened through about 0.71 mm and added to the cone blender. The blender contents were mixed for 20 minutes with the intensifier bar off. The magnesium stearate was screened through about 0.8 mm filter and was added to the cone blender. The mixture was blended for an additional five minutes with the intensifier bar off. One skilled in art will recognize that for the MCC and other fillers, the above process may be modified. One skilled in art will recognize that alternated addition and mixing methods are also acceptable.

During the process of manufacturing the tablets, before the compression into tablet form, an initial batch of blended product was blended for 2 hours, with samples obtained throughout the time period. The samples were tested for segregation.

Compression of tablets. The blend was compressed using a rotary tablet press. Tablets were compressed at different compression forces ranging from 5 to 25 Kp and tested for physical properties hardness, dissolution, thickness, friability, and content uniformity. For dissolution tests, tablets of different hardness were tested using USP Apparatus II using 900 ml of pH 1.2 buffer. The tablets were passed through a tablet deduster and metal checker after compression. The tablets were then coated in a perforated coating pan.

Tests were also conducted to study the effect of coating on dissolution and stability. Tablets were coated with Opadry (containing hydroxypropyl methylcellulose) material. A dissolution testing apparatus at 100 rpm was used to generate results. Alternate dissolution methods, e.g. 50 rpm using appropriate USP apparatus is also acceptable. Samples were collected after various levels of weight gain (based on amount of coating) and tested for dissolution at 15, 30, and 45 minutes. To determine the stability, coated tablets were put in a chamber under 40° C./75% RH accelerated conditions in an open dish for three months. Dissolution testing was carried out at 15, 30, and 45 minutes.

Near IR Spectroscopy. A near infrared (near IR) for memantine immediate release formulation was performed with Infrared Chemical Imaging System (Spectral Dimension, Olney, Md.). The tablet cross-section was measured, and single channel image at 1692 nm was used as a marker for memantine. The memantine rich domain was measured showing the distribution of the active ingredient. Different lots of memantine immediate release tablets were analyzed in triplicate. The analysis of data showed that memantine distribution among different lots was similar.

Results and Discussion

The samples obtained during the 2-hour blending test exhibited no noticeable deblending. The results showed that the formula ingredients allowed for good distribution of the active ingredients and that, once blended, the active ingredient remained uniformly distributed throughout the tablet matrix. The mixing time of 20 minutes (400 revolutions) was chosen as the preferred blending time. A lack of significant shifts in particle size distribution were observed regardless of blend time, indicating that no measurable particle attrition took place during blending. The results were well within the limits of the USP content uniformity test for tablets.

The results of the effect of compression force on tablet hardness showed that as compression force (kN) increased, a linear increase in tablet hardness (Kp) also occurred. Similarly, as compression force increased, there was a linear decrease in tablet thickness (inches). One unfavorable development during compression was the appearance of tablet sticking. Lower punches were embossed with the tablet strength (5, 10 or 20) and upper punches with "FP". Sticking to the punches, particularly the "P", was observed at lower compression forces. Producing harder tablets eliminated the sticking issue.

The effect of tablet hardness on dissolution was evaluated further. The data showed that hardness has an effect on dissolution. This effect was only observed for the 15 minutes time point, which relates to the disintegration of the tablets. Complete release was obtained for the 30 minutes time point. The proposed dissolution specification for the product was no less than 80% dissolved in 30 minutes. Based on the data, the higher tablet hardness required to avoid sticking will have no effect on the dissolution specification. The data for hardness and dissolution values is present in Tables 5a and 5b and Tables 6a and 6b below.

TABLE 5

Dissolution of memantine HCl uncoated core tablets of different hardness

| Strength mg | 5 mg | 10 mg | | 15 mg | | 20 mg | |
|---|---|---|---|---|---|---|---|
| Hardness (Kp) | 10(4-10) | 7 | 13 | 12 | 14 | 12 | 20 |
| Time (min) | | | | % Dissolved | | | |
| 15 | 52 | 99 | 79 | 97 | 74 | 100 | 34 |
| 30 | 97 | 99 | 96 | 101 | 103 | 100 | 97 |
| 45 | 98 | 99 | 96 | 100 | 102 | 100 | 99 |

TABLE 5b

Dissolution of Neramexane Mesylate Core Tablets of different hardness (Filler lactose-free)

| Strength mg | 12.5 mg | | 25 mg | | 50 mg | |
|---|---|---|---|---|---|---|
| Lot # RD- | 0943-1B | | 0903-144A | | 0903-144C | |
| Hardness (Kp) | 6 kp | 11 kp | 13 kp | 22 kp | 21 kp | 35 kp |
| Time (min) | | | % Dissolved | | | |
| 15 | 105 | 104 | 96 | 96 | 101 | 99 |
| 30 | 106 | 107 | 101 | 99 | 109 | 103 |
| 60 | 102 | 105 | 101 | 100 | 110 | 107 |

TABLE 6

Dissolution of memantine HCl coated tablets, different hardness

| | Strength | | | |
|---|---|---|---|---|
| | 5 mg | 10 mg | 15 mg | 20 mg |
| | | Core tablets Hardness (Kp) | | |
| Time (min.) | 4-10 | 7-13 | 10-16 | 12-20 |
| | | % Dissolved | | |
| 15 | 96 | 92 | 94 | 96 |
| 30 | 98 | 99 | 97 | 101 |
| 45 | 97 | 98 | 97 | 102 |

TABLE 6b

Dissolution of Neramexane Mesylate Coated Tablets

| Strength | 12.5 mg | 25 mg |
|---|---|---|
| Lot # RD- | 1033-29A | 1033-4A |
| Core table hardness (Kp) | 7-9 | 16-18 |
| | % Dissolved | |
| 15 min | 100 | 103 |
| 30 min | 102 | 103 |
| 60 min | 102 | 103 |

Tablet friability was tested since the product was film-coated to mask the characteristic taste of the drug. Generally, the friability values were very low, indicating good mechanical integrity for the tablets. Tablet content was reviewed for uniformity, and in all cases tablets had low variability in content.

Initial dissolution testing was also conducted. Memantine HCl is a highly soluble and highly permeable drug. A target dissolution of no less than 80% in 30 minutes was desired in order to support a Biopharmaceutical Classification System (BCS) Class 1 classification for the drug. Tablets also showed rapid dissolution (greater than 80% in 30 minutes) even at very high hardness (20 Kp for 20 mg tablets).

Study results also showed that the coating process and the coating level had no effect on dissolution and stability of the final products. No significant changes were observed after three months under the extreme conditions, demonstrating the stability of the formulations. The dry blend process designed is very resistant to blend segregation and it is not sensitive to particle size distribution of the active or blend. The tablets showed good mechanical integrity (with compression force of 10 kN for 5 mg tablets) and good content uniformity. Two methods were used to reduce the agglomeration of memantine particles: 1) increase ratio of diluents to the drug, thereby reduce available path for interaction; 2) by mixing active and diluents for an appropriate time.

Example 2

Pharmacokinetic Study of Memantine

The present example presents the bioavailability of immediate release memantine tablets as compared to modified release memantine tablets.

Materials and Methods

The study design in the present example was a 57-day single-center, open-label study in 24 young healthy subjects, ages ranging from 18 to 35 years old. Subjects underwent a screening evaluation consisting of a complete medical history, complete physical examination with vital signs, 12-lead ECG, clinical laboratory evaluations, consisting of a CBC (including differential), clinical chemistry, urinalysis, RPR/VDRL, Anti HIV 1 and 2 tests, drugs of abuse screen (including alcohol and nicotine), Anti-HCV and HbsAg. Female subjects had a β-hCG serum pregnancy test performed at screening and a urine pregnancy test on Day −1.

Inclusion criteria included informed consent, normal physical examination, healthy adults between 18 and 35 years of age, non-smokers, within 15% of ideal body weight in relation to height, and a sitting pulse rate of not less than 50 beats per minute by palpitation, and a heart rate of not less than 50 beats per minute as recorded by ECG. Exclusion criteria included hypersensitivity to memantine or other NMDA antagonists, presence of any clinically significant disease, sitting systolic blood pressure greater than 180 mmHg or less than 100 mmHg or a sitting diastolic blood pressure greater than 100 mmHg or less than 60 mmHg at screening, significant ECG abnormalities, history of alcohol or substance abuse, positive tests to drugs of abuse, consumption of caffeine within 48 hours or alcohol within 72 hours prior to testing, participation in other clinical investigation within 30 days of study, clinical conditions associated with memantine, concomitant medications, or females breastfeeding.

There were three treatment regimens including an immediate release (IR) memantine HCl 10 mg tablet (30 minutes dissolution, i.e., Treatment A), a modified release (MR) memantine HCl 20 mg tablet (formulation I, 6 Hour Dissolution, i.e., Treatment B), and a second modified release memantine HCl 20 mg tablet (formulation II, 12 hour dissolution, i.e. Treatment C). The modified release formulations contained different compositions to achieve release rates>70% drug release in about 6 hour and about 12 hours.

The subjects received three treatments on study days 1, 22, and 43 in a crossover manner separated by a 21-day washout period based on randomized treatment sequences. The immediate release treatment was administered on Day 1 at 0800 and 1200 hours. The modified release treatments were administered on Day 1 at 0800 hours. After the washout periods, the subjects were crossed over to the other treatment (MR or IR). Formulations B and C are discussed in detail in co-pending application Ser. No. 11/155,330 filed simultaneously with the present application.

Subjects were admitted into a non-smoking environment at approximately 1900 hours on Days −1, 21, and 42. There were a total of six overnight stays for each subject (Days −1, 1, 21, 22, 42 and 43). Subjects were subjected to diet and fluid control and received no concomitant medications.

Vital signs and adverse events were recorded over the course of the study. Blood samples for the determination of memantine were obtained from each subject during the course of the study 1, 22, and 43 on study day after the 0800 hour drug administration at the following times: 0.0 hour (pre-dose), every hour for the first 12 hours, 14, 24, 36, 48, 72, 96, 144, 192, 240, 288 and 336 hours post dose. Approximately 390 mL of blood were collected during the course of this study from each subject (including pre-study, post-study and follow-up clinical analysis). A total of 72 plasma samples were collected during the study for pharmacokinetic analysis. Blood samples for the determination of memantine concentration were collected by a qualified phlebotomist using pre-chilled 5 mL green top Vacutainer® tubes (containing sodium heparin as an anticoagulant).

Approximately 5 mL of blood were collected directly into pre-chilled 5-mL green top Vacutainer® tubes (containing sodium heparin) following dosing on Days 1, 22, and 43. Blood samples were centrifuged within 30 minutes from the time of draw at 2,500 g for 10 minutes at 4° C. and the plasma was harvested and transferred into pre-chilled, Forest coded polypropylene tubes. The samples were then flash frozen in an isopropyl alcohol/dry ice bath and stored in a −70° C. freezer.

Bioanalytical procedures. The bioanalytical procedure used to measure the plasma memantine concentrations was validated to demonstrate accuracy, linearity, reproducibility, and precision of the analytical procedures. An LC/MS/MS (liquid chromatography/mass spec/tandem mass spec) method was developed for the determination of memantine in human plasma. After the addition of 10 ng of [$^2H_6$] memantine internal standard and 0.5 M sodium carbonate buffer to plasma standards and samples, the compounds were extracted with ethyl acetate. The organic layer was isolated and dried at room temperature under the vacuum in a sample concentrator (Savant). The dry residue was analyzed after reconstitution in mobile phase. The components of the reconstituted samples were separated on a Zorbax SB-C8 column (150×4.6 mm, 3.5 μm) and detected by atmospheric pressure chemical ionization (APCI) with a selected reaction monitoring (SRM) positive ion mode. The SRM used precursor→positive product ions of m/z 180→163 and m/z 186→169 to monitor memantine and its internal standard, respectively. The protonated molecular ions of memantine and [$^2H_6$] memantine are the precursor ions for the SRM mode. The peak height ratio of memantine product ion to that of its internal standard was the response used for quantification. The plasma standards of the method validation showed accuracy within ±8.2% deviation and precision did not exceed 7.6% CV. Accuracy for the determination of memantine in plasma quality controls was within ±8.8% deviation with a precision not exceeding 9.8% CV. The lower limit of quantification of the method was 0.5 ng/mL.

Pharmacokinetic analysis. Pharmacokinetic parameters were estimated using WinNonlin (version 3.3, Pharsight Corporation, Mountain View, Calif.). The following parameters were determined from the plasma concentrations of memantine following single dose administration: the area under the plasma concentration time curve ($AUC_{0-t}$, $AUC_{0-24}$, and $AUC_\infty$), maximum plasma concentration ($C_{max}$), time of maximum plasma concentration ($T_{max}$), elimination half-life ($T_{1/2}$) and mean residence time (MRT). Maximum plasma concentrations ($C_{max}$) and the time of the maximum concentration ($T_{max}$) for memantine were determined by observation.

The first-order rate constant, $\lambda_z$, describing the terminal decline in plasma was estimated by WinNonlin (version 3.3) using log-linear regression of the terminal linear phase of the mean plasma concentration-time curves of memantine.

Estimates of terminal elimination half-life ($T_{1/2}$) in hours were calculated with equation 1:

$$T_{1/2} = \frac{0.693}{\lambda_z} \quad \text{Eq. 1}$$

The area under the plasma concentration versus time curve up to the last measurable concentration at time t ($AUC_{0-t}$) or at 24 hours ($AUC_{0-24}$) was estimated by numerical integration using the linear trapezoidal rule (Equation 2).

$$AUC_{0-t} = \sum_{i=2}^{n} 0.5 \cdot (C_i + C_{i-1}) \cdot (t_i - t_{i-1}) \quad \text{Eq. 2}$$

where $C_i$ was the plasma concentration at the corresponding sampling time point $t_i$.

Area under the plasma concentration-time curve up to time infinity ($AUC_{0-\infty}$) of memantine was computed using the following (Equation 3):

$$AUC_{0-\infty} = AUC_{0-t} + \frac{C_{last}}{\lambda_z} \quad \text{Eq. 3}$$

where $C_{last}$ is the last measurable concentration in the concentration-time profile.

MRT was calculated using the following (Equation 4):

$$MRT = \frac{AUMC}{AUC_{0-\infty}} \quad \text{Eq. 4}$$

where AUMC is the area under the first moment curve.

Descriptive statistics for the memantine pharmacokinetic parameters $C_{max}$, $T_{max}$, $AUC_{0-t}$, $AUC_{0-24}$, $AUC_{0-\infty}$, $t_{1/2}$, and MRT were provided for subjects who completed the study.

Results

Adverse events. There were no serious adverse events reported. Nineteen (82.6%) of the twenty-three subjects reported a total of 42 treatment emergent adverse events following administration of Treatments A, B, and C. There were no differences in the number of adverse events observed with treatment. A total of 14, 12, and 16 adverse events were observed following Treatments A, B, and C, respectively. The most common adverse events (i.e., occurring in 3 or more subjects) were headache, dizziness, flatulence, and infection.

Figure 2:
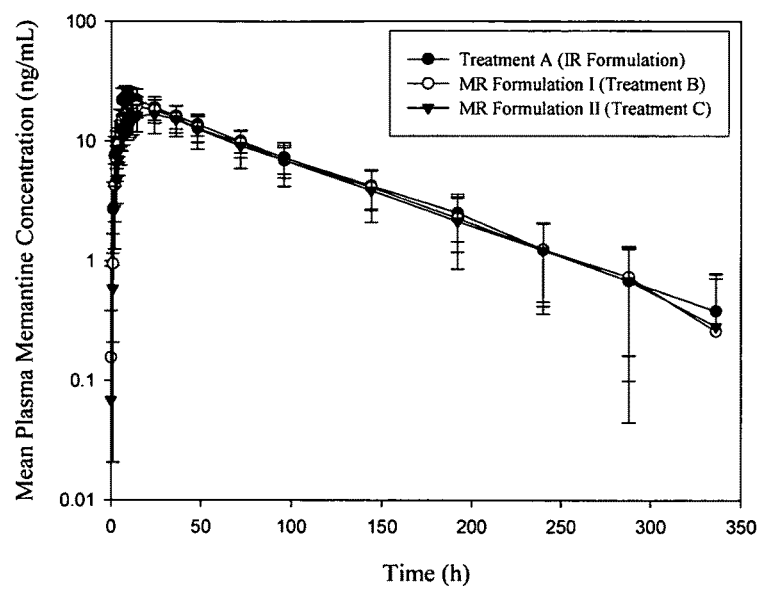
FIG. 2 is a plot of the log of the mean plasma concentrations of memantine (ng/mL) following administration of two-10 mg memantine HCl immediate release tablets four hours apart (Treatment A, 30 min release) (closed circle), or modified release tablets (Treatments B and C, 6 hour and 12 hour release) tablets (open circle and inverted triangle), in young healthy male and female subjects against time elapsed (hours) from administration.
Figure 3:
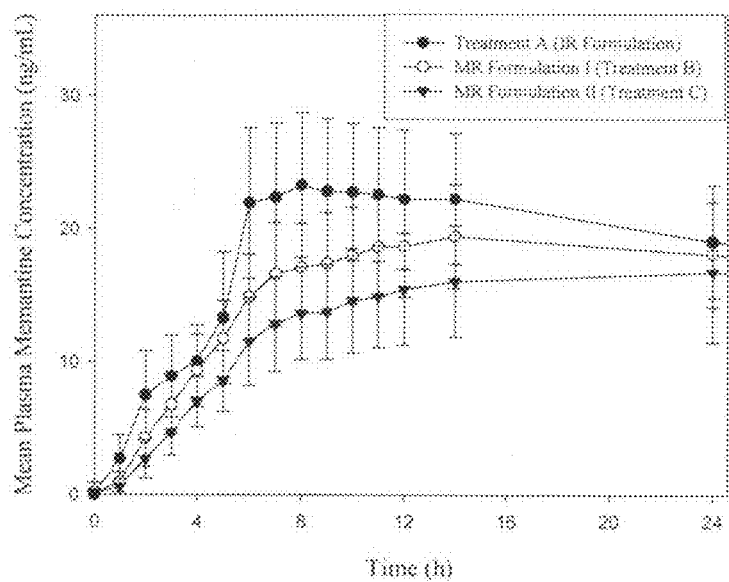
FIG. 3 is a plot of mean plasma concentrations of memantine (ng/mL) following administration of two 10 mg memantine HCl immediate release tablets of the present invention four hours apart (Treatment A) (closed circle) or modified release tablets prepared using a matrix formula containing HPMC (Treatments B and C) (open circle and inverted triangle) in young healthy male and female subjects against time (hours) for the first 24 hours following administration.
Figure 4:
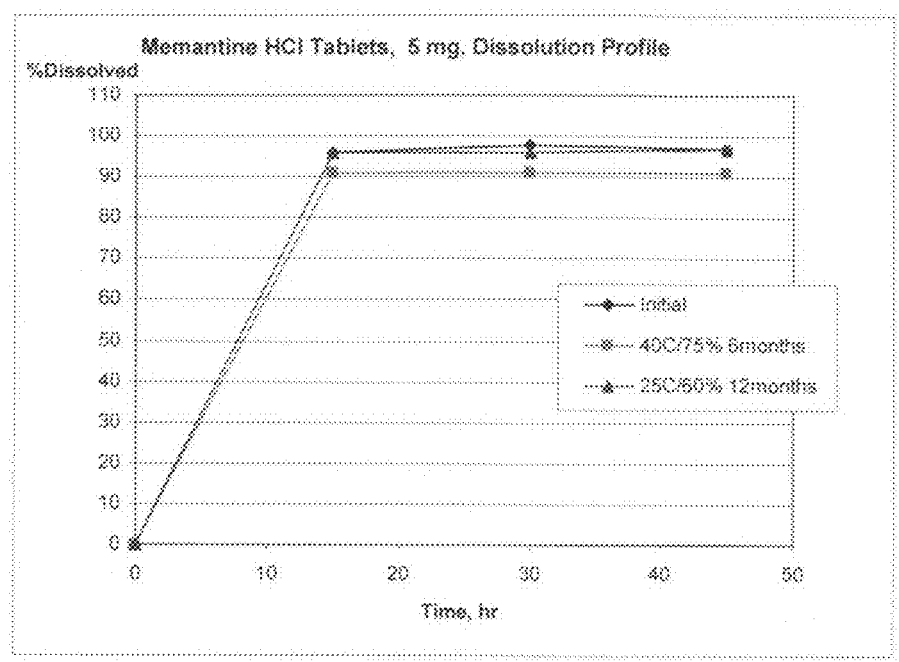
FIG. 4 depicts the dissolution of 5 mg memantine HCl tablets. Dissolution is shown as the percent dissolved over time (hours).
Figure 5:
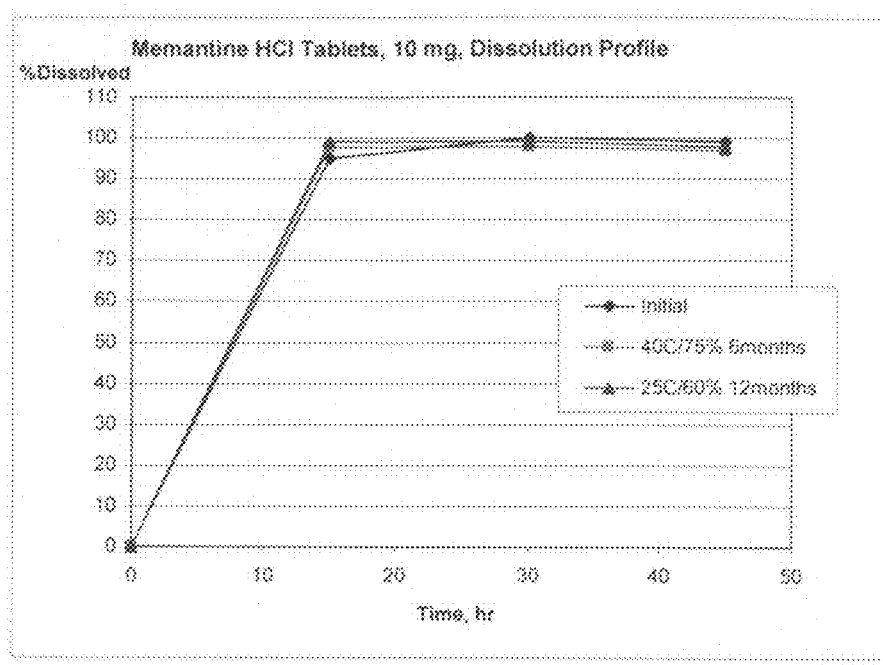
FIG. 5 depicts the dissolution of 10 mg memantine HCl tablets. Dissolution is shown as the percent dissolved over time (hours).
Figure 6:
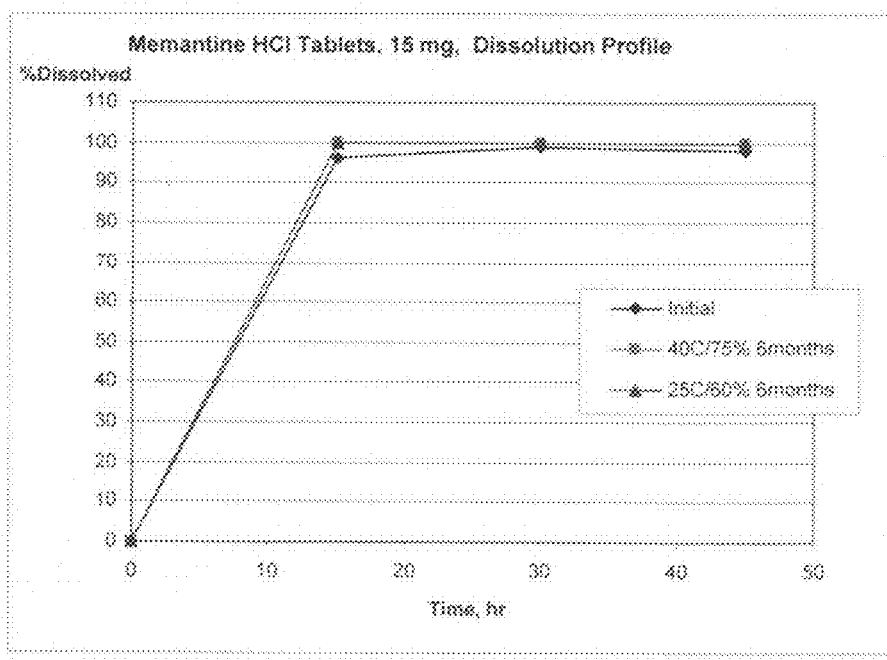
FIG. 6 depicts the dissolution of 15 mg memantine HCl tablets. Dissolution is shown as the percent dissolved over time (hours).

Pharmacokinetic results. The mean plasma concentrations of memantine are illustrated in FIG. 1 (linear scale) and in FIG. 2 (semi-log scale). The plots in FIGS. 1 and 2 show results of three treatments. The differences are further depicted in FIG. 3. FIG. 3 depicts mean plasma concentrations of memantine during the first 24 hours post-dose. Peak memantine concentration was highest following administration of the IR formulation (Treatment A) and lowest following administration of the MR formulation II (Treatment C).

The mean (±SD) pharmacokinetic parameters of memantine following Treatments A, B and C are listed below in Table 7.

TABLE 7

| Parameter | Treatment A IR Formulation I (n = 20) | Treatment B MR Formulation I (n = 20) | Treatment C MR Formulation II (n = 20) |
|---|---|---|---|
| $C_{max}$ (ng/mL) | 24.92 ± 4.82 | 20.37 ± 3.83 | 17.48 ± 4.60 |
| $T_{max}$ (h) | 8.2 ± 2.0 | 12.1 ± 2.1 | 19.3 ± 7.3 |
| $AUC_{0-24}$ (ng · h/mL) | 435.7 ± 87.0 | 367.2 ± 66.8 | 303.3 ± 78.2 |
| $AUC_{0-t}$ (ng · h/mL) | 1898.2 ± 453.0 | 1755.7 ± 468.9 | 1653.8 ± 589.8 |
| $AUC_{0-\infty}$ (ng · h/mL) | 1969.0 ± 455.8 | 1828.0 ± 489.9 | 1730.1 ± 609.4 |
| $T_{1/2}$ (h) | 57.4 ± 14.2 | 59.6 ± 15.4 | 59.1 ± 15.5 |
| MRT (h) | 83.9 ± 17.8 | 87.4 ± 19.4 | 89.0 ± 20.2 |

Statistical comparisons of memantine parameters are presented below in Table 8.

TABLE 8

| Parameter | Treatment B vs. Treatment A | | Treatment C vs. Treatment A | |
|---|---|---|---|---|
| | Least-Squares Means Ratio | 90% Confidence Interval | Least-Squares Means Ratio | 90% Confidence Interval |
| $C_{max}$ | 81 | 76.65-85.75 | 70 | 65.93-73.77 |
| $AUC_{0-24}$ | 84 | 80.23-87.79 | 69 | 66.00-72.22 |
| $AUC_{0-t}$ | 91 | 83.90-99.10 | 84 | 77.15-91.14 |
| $AUC_{0-\infty}$ | 92 | 84.29-99.04 | 85 | 78.06-91.73 |

Absorption of memantine from the modified release tablets was delayed as compared to the immediate release tablet. The rate and extent of absorption of memantine were reduced following administration of the modified release formulations as compared to the immediate release formulation. Importantly, the rate of absorption ($T_{max}$) was delayed from 8.2 hours for the IR Tablets (i.e., BID administered about 4 hours after the administration of the first tablet to 12.1 hours and 19.3 hours for modified release tablets I and II, respectively).

The 90% confidence intervals for the comparison of the log-transformed $C_{max}$, $AUC_{0-24}$, $AUC_{0-t}$ and $AUC_{0-\infty}$ for Treatment A (IR tablet) versus Treatment B (MR Formulation I) showed a significant higher mean $C_{max}$ value but not in the AUC parameter values. The 90% confidence intervals for the comparison of the log-transformed $C_{max}$, $AUC_{0-24}$, $AUC_{0-t}$ and $AUC_{0-\infty}$ for Treatment A (IR tablet) versus Treatment C (MR Formulation II) was significantly higher in mean $C_{max}$ and AUC values. These results demonstrate that IR tablets improved bioavailability as compared to modified release formulations.

There were no statistically significant gender effects on elimination half-life and weight-adjusted $C_{max}$, $AUC_{0-t}$ and $AUC_{0-\infty}$ values following administration of the IR formulation.

Discussion

In this study, single daily doses of 20 mg memantine, administered as two-10 mg doses of an immediate release tablet, separated by a 4-hour interval, were found to be safe and well-tolerated. There were no serious adverse events observed in this study.

The rate and extent of absorption of memantine was highest following administration of the immediate release tablets. $C_{max}$ values averaged 24.92, 20.37 and 17.48 ng/mL for the immediate release tablet (Treatment A, 30 minutes release), the modified release tablet formulation I (Treatment B, 6 hour release) and the modified release tablet formulation II (Treatment C, 12 hour release), respectively. $AUC_{0-\infty}$ averaged 1969, 1827 and 1730 ng·h/mL for the immediate release tablet (Treatment A), the modified release tablet formulation I (Treatment B) and the modified release tablet formulation II (Treatment C), respectively. Mean $T_{max}$ was 8.2 hours, 12.1 hours and 19.3 hours, for Treatments A, B and C, respectively. The delayed $T_{max}$ for the two modified-release formulations is indicative of the slower absorption rate compared to the immediate-release tablets. These results demonstrate that the desired release characteristics were obtained for both the modified and immediate release formulations.

Example 3

Preparation of Memantine HCl 30-Minute Immediate Release Tablets

The present example demonstrates the makeup of 30-minute immediate release memantine tablets, with and without lactose monohydrate.

The methods of making the tablets are the same as those disclosed in Example 1. Specifically, the tablets are made of the following active components, coating agent, and other excipients as presented below in Tables 9 and 10. Tables 9 and 10, summarizing the tablets with lactose monohydrate, contain the same data expressed respectively in absolute (mg) or relative (% w/w) terms.

TABLE 9

30 min release tablets with lactose monohydrate/MCC (weights in mg/tablet)

| Component/ Ingredient (mg) | Preferred Ranges | | Exact Composition (mg) | | | |
|---|---|---|---|---|---|---|
| Memantine HCl | 5.0 | 80.0 | 5.0 | 10.0 | 15.0 | 20.0 |
| Microcrystalline Cellulose | 23.4 | 458.5 | 26.1 | 52.1 | 78.2 | 104.2 |
| Lactose Monohydrate | 78.6 | 1537.9 | 87.4 | 174.8 | 262.1 | 349.5 |
| Colloidal Silicone Dioxide | 0.6 | 11.1 | 0.6 | 1.3 | 1.9 | 2.5 |
| Talc | 5.0 | 98.0 | 5.6 | 11.2 | 16.7 | 22.3 |
| Magnesium Stearate | 0.3 | 6.5 | 0.4 | 0.8 | 1.1 | 1.5 |
| Hydroxypropyl methylcellulose (Coating) | 3.4 | 66.0 | 3.8 | 7.5 | 11.3 | 15.0 |
| Total | 116.4 | 2258.0 | 128.8 | 257.5 | 386.3 | 515.0 |

For the dose proportional formulations of Table 10, the percentage ranges for each ingredient are identified in Table 9.

TABLE 10

Weights in % w/w of tablet with lactose monohydrate

|  | Preferred (Range) | % w/w | Exact % w/w |
|---|---|---|---|
| Memantine HCl (mg) | 3.5 | 4.3 | 3.9 |
| Microcrystalline Cellulose | 18.2 | 22.2 | 20.2 |
| Lactose Monohydrate | 61.1 | 74.7 | 67.9 |
| Colloidal Silicone Dioxide | 0.5 | 0.6 | 0.5 |
| Talc | 3.9 | 4.7 | 4.3 |
| Magnesium Stearate | 0.3 | 0.3 | 0.3 |
| Hydroxypropyl methylcellulose (Coating) | 2.6 | 3.2 | 2.9 |
| Total | — | — | 100 |

Tables 11 and 12, summarizing the tablets without lactose, contain the same data expressed respectively in absolute (mg) or relative (% w/w) terms.

TABLE 11

30 min release tablets lactose free (weights in mg/tablet)

| Excipient | Preferred ranges | | Exact Composition (mg) | | | |
|---|---|---|---|---|---|---|
|  |  |  | 5 mg | 10 mg | 15 mg | 20 mg |
| Memantine HCl | 5.0 | 80.0 | 5.0 | 10.0 | 15.0 | 20.0 |
| Microcrystalline Cellulose (ProSolv) | 87.8 | 1716.0 | 97.5 | 195.0 | 292.5 | 390.0 |
| Croscarmellose Sodium | 2.0 | 38.7 | 2.2 | 4.4 | 6.6 | 8.8 |
| Talc | 4.5 | 88.0 | 5.0 | 10.0 | 15.0 | 20.0 |
| Mg Stearate | 0.3 | 5.3 | 0.3 | 0.6 | 0.9 | 1.2 |
| Opadry (contiaing Hydroxypropyl methylcellulose) Coating) | 3.0 | 58.1 | 3.3 | 6.6 | 9.9 | 13.2 |
| Total | 102.5 | 1986.1 | 113.3 | 226.6 | 339.9 | 453.2 |

For the dose proportional formulations of Table 11, the percentage ranges for each ingredient are identified in Table 12.

TABLE 12

Weights in % w/w of tablet

|  | Preferred Range | % w/w | Exact % w/w |
|---|---|---|---|
| Memantine HCl (mg) | 4.0 | 4.8 | 4.4 |
| Silicified Microcrystalline Cellulose (ProSolv SMCC 90) | 77.5 | 94.7 | 86.1 |
| Croscarmellose Sodium | 1.7 | 2.1 | 1.9 |
| Talc | 4.0 | 4.8 | 4.4 |
| Mg Stearate | 0.3 | 0.3 | 0.3 |
| Hydroxypropyl methylcellulose Opadry (Coating) | 2.6 | 3.2 | 2.9 |
| Total | — | — | 100.00 |

Figure 7A:
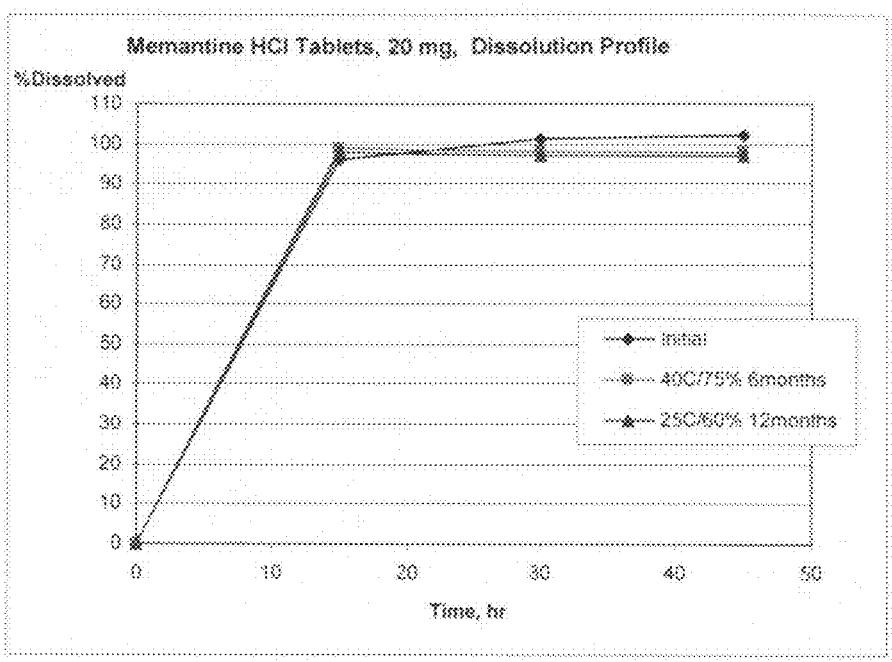
FIG. 7a depicts the dissolution of 20 mg memantine HCl tablets, Lot A. Dissolution is shown as the percent dissolved over time (hours).
Figure 7B:
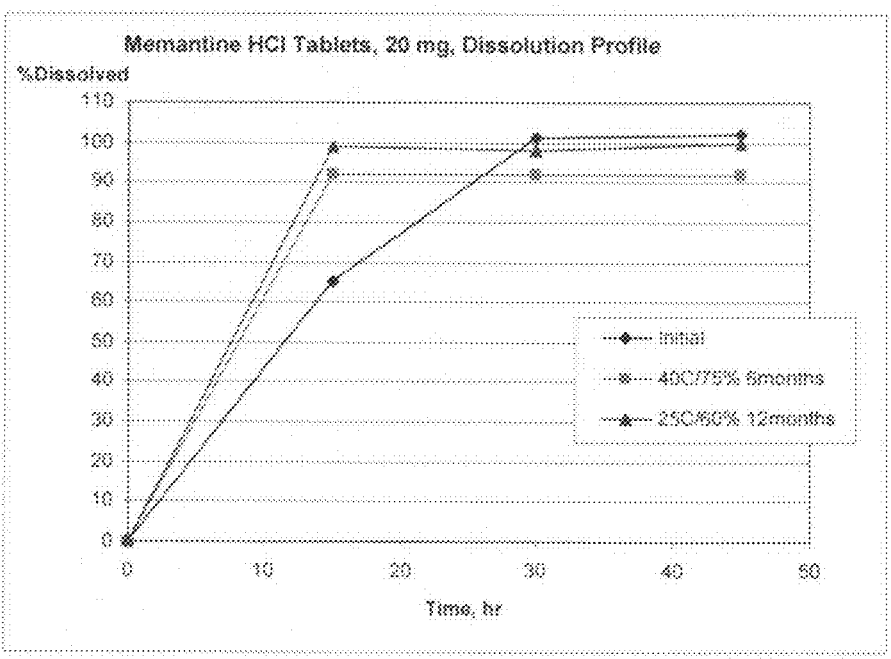
FIG. 7b depicts the dissolution of 20 mg memantine HCl tablets, Lot B. Dissolution is shown as the percent dissolved over time (hours).
Figure 8:
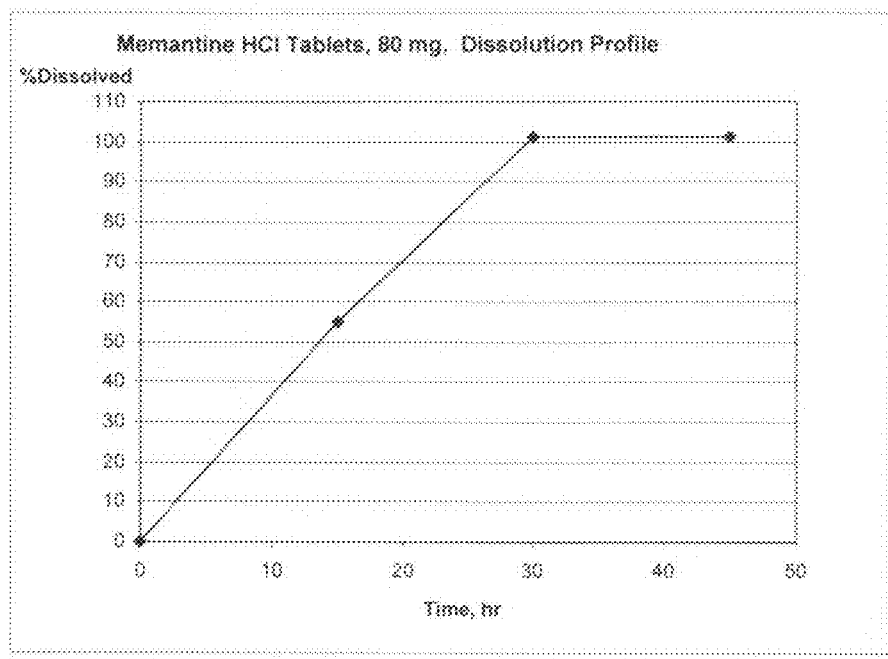
FIG. 8 depicts the dissolution of 80 mg memantine HCl tablets. Dissolution is shown as the percent dissolved over time (hours).
Figure 9:
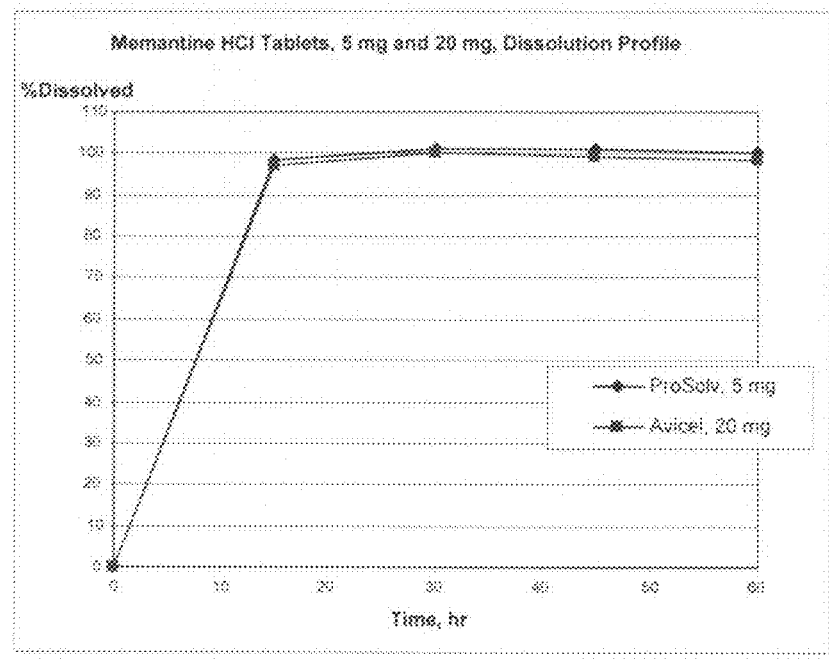
FIG. 9 plots the dissolution of memantine with microcrystalline cellulose (i.e., without lactose) at a 5 mg strength using Prosolv® (a mixture of microcrystalline cellulose and colloidal silicone dioxide) and at a 20 mg strength using Avicel® (microcrystalline cellulose) against time (hours) from administration.

FIGS. 4, 5, 6, 7, and 8 show dissolution of 30 minutes IR tablets for 5 mg, 10 mg, 15 mg, two lots of 20 mg and 80 mg respectively for the formulation containing lactose monohydrate and MCC. FIG. 9 shows the dissolution of 5 mg and 20 mg lactose-free formulations. In FIG. 7, another lot of 20 mg shows 15 minutes is about 65% at initial time point, but greater than 80% on stability. This variation is lot to lot variation. The results show that greater than 80% of the drug is released in 30 minutes and in many instances greater than 80% of the drug is released in 15 minutes.

Adduct Formation. An adduct is formed as a result of reaction between memantine with lactose monohydrate and similar excipients, known as reducing sugars. The adduct is not formed in lactose-free/MCC alone formulations. The adduct formation is detected using HPLC method with an Evaporative Light Scattering Detector. The product stored at ambient conditions over 40 months contained the adduct level of up to about 2.5%. The adduct data are presented in Table 13.

TABLE 13

| Strength | Interval/Condition | Adduct % | Formula |
|---|---|---|---|
| 5 mg | 7 months Ambient | 0.61 | Lactose/MCC |
| 5 mg | 36 months 25° C./60% RH | 2.32 | Lactose/MCC |
| 20 mg | 36 months 25° C./60% RH | 1.30 | Lactose/MCC |
| 20 mg | 5 months Ambient | 0.37 | Lactose/MCC |
| 5 mg | 3 months 40° C./75% RH | Non detected (<0.2%) | MCC (Lactose free) |
| 20 mg | 3 months 40° C./75% RH | Non detected (<0.2%) | MCC (Lactose free) |

It is determined that adduct level of less than about 3%, preferably less than about 2.5% are qualified in accordance with ICH guidelines Q3B(R), FDA Guidelines, Rockville, Md.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions; and protocols are cited throughout this application, the disclosures of which are incorporated herein by reference in their entireties for all purposes.

What is claimed:

1. An immediate release solid oral dosage form comprising a) between 2% w/w and 40% w/w of an active ingredient selected from neramexane, optical isomers, diastereomers, enantiomers, hydrates, and pharmaceutically acceptable salts thereof; b) between 2% w/w to 7% w/w of hydroxypropyl methylcellulose; c) between 60% w/w and 90% w/w of microcrystalline cellulose; d) between 0.5% w/w and 3% w/w of colloidal silicon dioxide; e) between 0.5% w/w and 2% w/w of talc; f) between 0% w/w and 2% w/w of magnesium stearate and g) between 2% w/w and 5% w/w of croscarmellose sodium;

said dosage form exhibiting dose-proportionality and releasing said active ingredient at a rate of more than about 80% within about the first 60 minutes following entry of said form into a use environment, wherein: said dosage form exhibits an average $T_{max}$ within the range of about 2 to about 8 hours with an active ingredient load within the range of about 2.5 to about 150 mg, and wherein said dosage form is free of lactose.

2. The immediate release solid oral dosage form according to claim 1 wherein said oral dosage form releases said active ingredient at a rate of more than about 80% within the first 30 minutes following entry of said form into a use environment.

3. The immediate release solid oral dosage form according to claim 2 wherein said oral dosage form releases said active ingredient at a rate of more than about 80% within the first 15 minutes following entry of said form into a use environment.

4. The immediate release solid oral dosage form according to claim 1, wherein said active ingredient is neramexane mesylate.

5. The immediate release solid oral dosage form according to claim 4, wherein the active ingredient is present in an amount within the range from about 2% w/w to about 20% w/w.

6. The immediate release solid oral dosage form according to claim 5, wherein the active ingredient is present in an amount within the range from about 3.2% w/w to about 10% w/w.

7. The immediate release solid oral dosage form according to claim 6, wherein the active ingredient is present in an amount within the range from about 3.9% w/w to about 8% w/w.

8. The immediate release solid oral dosage form according to claim 1, wherein the solid oral dosage form has a hardness within the range of between about 3 and about 40 Kp.

9. The immediate release solid oral dosage form according to claim 8, wherein the solid oral dosage form has a hardness within the range of between about 4 and about 30 Kp.

10. The immediate release solid oral dosage form according to claim 1, wherein the magnesium stearate is present in an amount within the range from about 0.2% to about 0.5% w/w.

11. The immediate release solid oral dosage form according to claim 1 wherein said solid oral dosage form is a tablet.

12. The immediate release solid oral dosage form of claim 1, wherein the solid oral dosage form further comprises a pharmaceutically acceptable coating.

13. The immediate release solid oral dosage form according to claim 12, wherein the pharmaceutically acceptable coating contains hydroxypropyl methylcellulose.

14. The immediate release solid oral dosage form according to claim 12, wherein the pharmaceutically acceptable coating contains a methacrylic acid-ethyl acrylate copolymer.

15. The immediate release solid oral dosage form according to claim 12, wherein the pharmaceutically acceptable coating is present in an amount within the range from about 2% w/w to about 7% w/w.

16. The immediate release solid oral dosage form according to claim 15, wherein the pharmaceutically acceptable coating is present in an amount within the range from about 2% w/w to about 5% w/w.

17. A method of treating a disorder selected from the group consisting of Parkinson's disease, AIDS dementia, neuropathic pain, cerebral ischemia, epilepsy, glaucoma, hepatic encephalopathy, multiple sclerosis, stroke, depression, tardive dyskinesia, malaria, Borna virus, and Hepatitis C, wherein the method consists of administering an immediate release solid oral dosage form of claim 1 to a patient suffering from such disorder.

18. The method of claim 17 wherein the immediate release solid oral dosage form is administered once daily.

19. The method of claim 17, wherein the immediate release solid oral dosage form is administered twice daily.

* * * * *